United States Patent
Ohsawa et al.

(10) Patent No.: US 9,809,645 B2
(45) Date of Patent: Nov. 7, 2017

(54) **ANTI-*STAPHYLOCOCCUS* ANTIBODY, METHOD FOR MANUFACTURING SAME, AND USAGE OF SAME**

(71) Applicants: ZENYAKU KOGYO KABUSHIKIKAISHA, Bunkyo-ku (JP); Juntendo Educational Foundation, Bunkyo-ku (JP)

(72) Inventors: Hiroyoshi Ohsawa, Nerima-ku (JP); Jumpei Enami, Nerima-ku (JP); Keiichi Hiramatsu, Bunkyo-ku (JP)

(73) Assignees: ZENYAKU KOGYO KABUSHIKIKAISHA, Bunkyo-ku (JP); Juntendo Educational Foundation, Bunkyo-ku (JP)

( * ) Notice: Subject to any disclaimer, the term of this patent is extended or adjusted under 35 U.S.C. 154(b) by 0 days.

(21) Appl. No.: 14/774,979

(22) PCT Filed: Mar. 11, 2014

(86) PCT No.: PCT/JP2014/056324
§ 371 (c)(1),
(2) Date: Sep. 11, 2015

(87) PCT Pub. No.: WO2014/142117
PCT Pub. Date: Sep. 18, 2014

(65) Prior Publication Data
US 2016/0024190 A1    Jan. 28, 2016

(30) Foreign Application Priority Data
Mar. 12, 2013 (JP) ................. 2013-049268

(51) Int. Cl.
| | | |
|---|---|---|
| A61K 39/395 | (2006.01) | |
| A61K 39/00 | (2006.01) | |
| A61K 39/38 | (2006.01) | |
| C07K 16/12 | (2006.01) | |

(52) U.S. Cl.
CPC .... C07K 16/1271 (2013.01); *A61K 2039/505* (2013.01); *A61K 2039/507* (2013.01); *C07K 2317/14* (2013.01); *C07K 2317/33* (2013.01); *C07K 2317/76* (2013.01)

(58) Field of Classification Search
CPC .............................. A61K 39/395; A61K 39/40
USPC .................... 424/130.1, 133.1, 184.1, 185.1
See application file for complete search history.

(56) References Cited

U.S. PATENT DOCUMENTS

2006/0115486 A1    6/2006  Pier et al.
2011/0236399 A1    9/2011  Mond et al.

FOREIGN PATENT DOCUMENTS

| WO | WO 03/059259 A2 | 7/2003 |
| WO | WO 03/063772 A2 | 8/2003 |
| WO | WO 2005/103084 A2 | 11/2005 |
| WO | WO 2011/008092 A2 | 1/2011 |

OTHER PUBLICATIONS

International Search Report dated Jun. 3, 2014 in PCT/JP2014/056324.
Tomás Maira-Litrán, et al., "Comparative Opsonic and Protective Activities of *Staphylococcus aureus* Conjugate Vaccines Containing Native or Deacetylated Staphylococcal Poly-N-Acetyl-β-(1-6)-Glucosamine" Infection and Immunity, vol. 73, No. 10, Oct. 2005, pp. 6752-6762 and 7789.
Marina L. Gening, et al., "Synthetic β-(1→6)-Linked N-Acetylated and Nonacetylated Oligoglucosamines Used to Produce Conjugate Vaccines for Bacterial Pathogens" Infection and Immunity, vol. 78, No. 2, Feb. 2010, pp. 764-772.
Casie Kelly-Quintos, et al., "Characterization of the Opsonic and Protective Activity against *Staphylococcus aureus* of Fully Human Monoclonal Antibodies Specific for the Bacterial Surface Polysaccharide Poly-N-Acetylglucosamine" Infection and Immunity, vol. 74, No. 5, May 2006, pp. 2742-2750.
Rebecca A. Brady, et al., "Identification of *Staphylococcus aureus* Proteins Recognized by the Antibody-Mediated Immune Response to a Biofilm Infection" Infection and Immunity, vol. 74, No. 6, Jun. 2006, pp. 3415-3426.
CDC, "*Staphylococcus aureus* Resistant to Vancomycin—United States, 2002" MMWR, vol. 51, No. 26, Jul. 5, 2002, pp. 565-567.
Sotirios Tsiodras, et al., "Linezolid resistance in a clinical isolate of *Staphylococcus aureus*" Lancet, vol. 358, Jul. 21, 2001, pp. 207-208.
R. Monina Klevens, et al., "Invasive Methicillin-Resistant *Staphylococcus aureus* Infections in the United States" JAMA, vol. 298, No. 15, Oct. 17, 2007, pp. 1763-1771.
CDC, "Four Pediatric Deaths from Community-Acquired Methicillin-Resistant *Staphylococcus aureus*—Minnesota and North Dakota, 1997-1999" MMWR, vol. 48, No. 32, Aug. 20, 1999, pp. 707-710.
Adam C. Schaffer, et al., "Staphylococcal Vaccines and Immunotherapies" Infect. Dis. Clin. North. Am., vol. 23, 2009, pp. 153-171.

(Continued)

*Primary Examiner* — Rodney P Swartz
(74) *Attorney, Agent, or Firm* — Oblon, McClelland, Maier & Neustadt, L.L.P.

(57) ABSTRACT

[Problem] The present invention addresses the problem of providing an anti-*Staphylococcus* antibody having preventive or therapeutic effects on staphylococcal infections. [Solution] Provided is an anti-*Staphylococcus* antibody having preventive or therapeutic effects on staphylococcal infections and a method for manufacturing said antibody, as well as a composition, a product, and a drug containing said antibody. The antibody is obtained by using deacetylated *Staphylococcus* for immunization.

19 Claims, 8 Drawing Sheets

(56) References Cited

OTHER PUBLICATIONS

Extended European Search Report dated Oct. 26, 2016 in Patent Application No. 14765434.7.
Ali I. Fattom, et al., "Antigenic Determinants of *Staphylococcus aureus* Type 5 and Type 8 Capsular Polysaccharide Vaccines," Infection and Immunity, American Society for Microbiology, vol. 66, No. 10, XP002153789, Oct. 1998, pp. 4588-4592.
Hiroyoshi Ohsawa, et al., "Successful selection of an infection-protective anti-*Staphylococcus aureus* monoclonal antibody and its protective activity in murine infection models," Microbiology and Immunology, vol. 59, No. 4, XP055311124, (2015), pp. 183-192.

[FIG. 1]
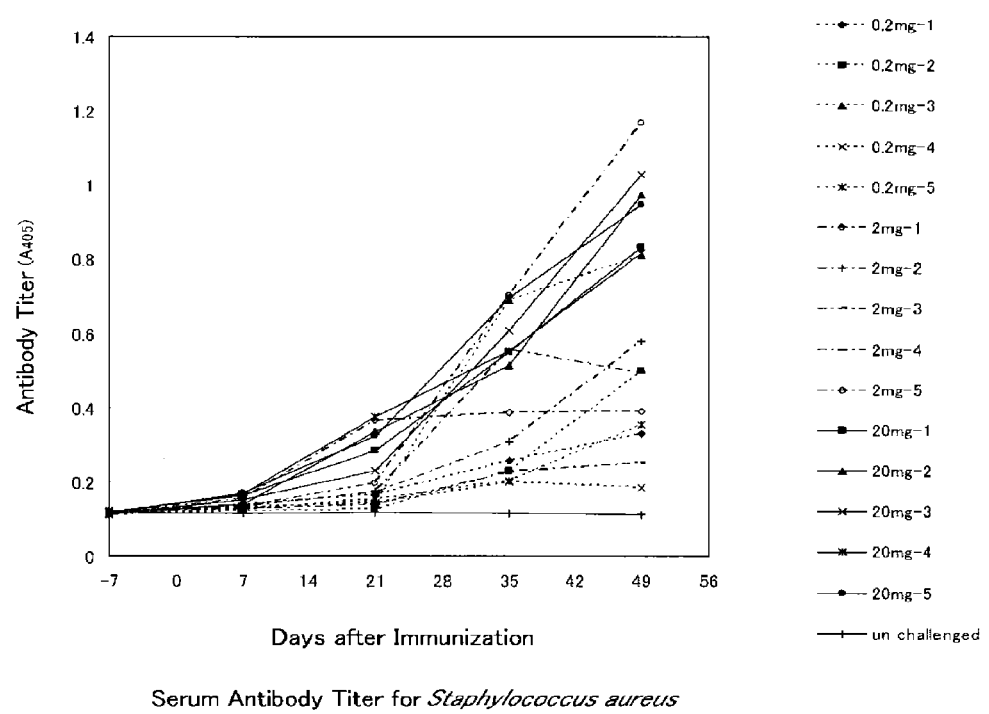
Serum Antibody Titer for *Staphylococcus aureus*

[FIG. 2]
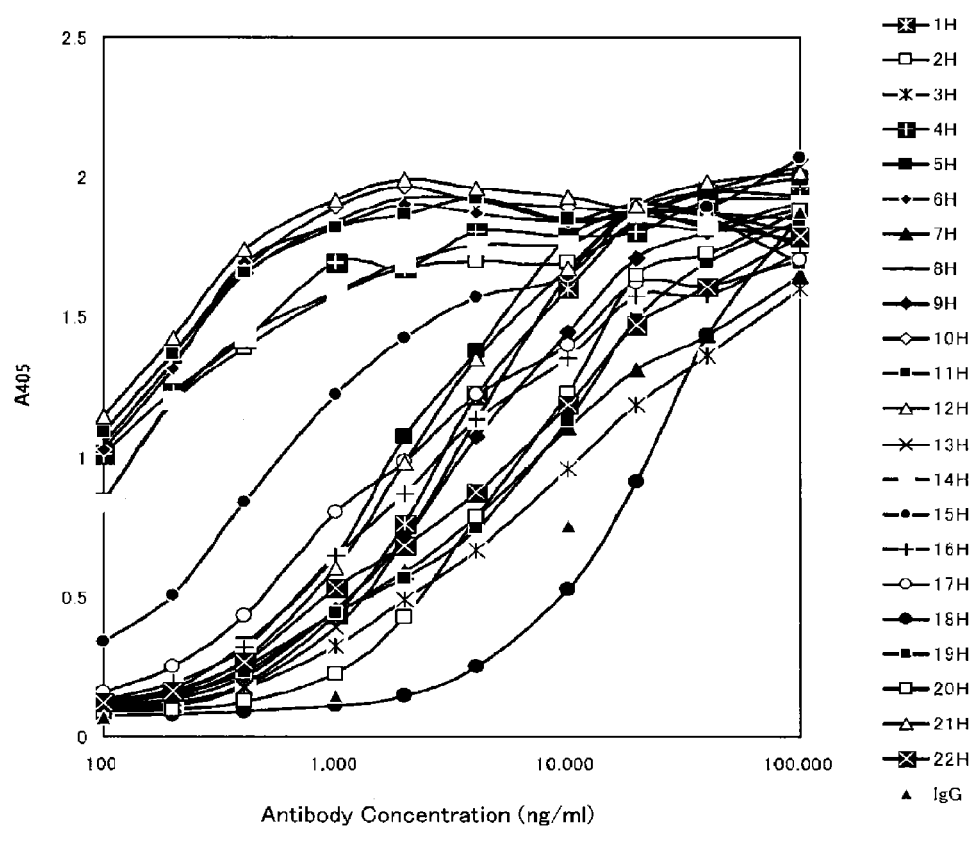
ELISA Reactivity of Anti-*Staphylococcus* Antibody

[FIG. 3]
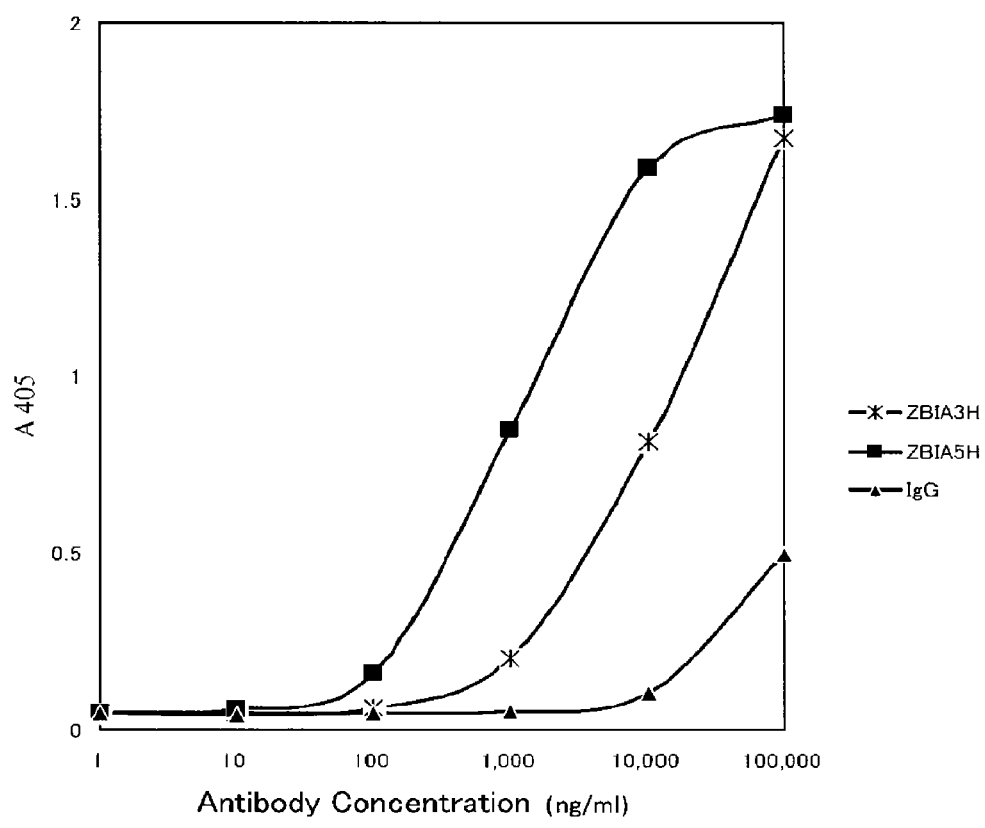
Reactivity of ZBIA5H Antibody and ZBIA3H Antibody
in *Staphylococcus epidermidis* Solid Phase Cell-ELISA

[FIG. 4]
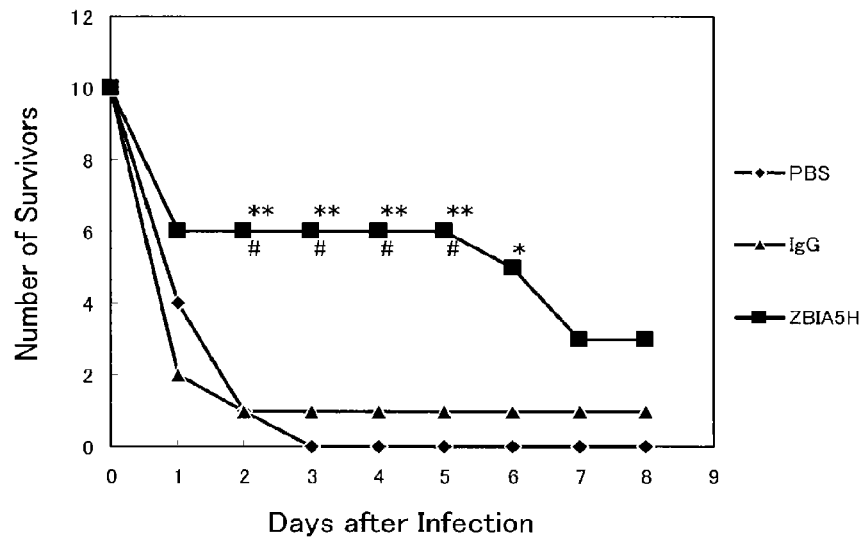
Effect of ZBIA5H Antibody in a Strain MW2 Induced Mouse Sepsis Model
[FIG. 5]
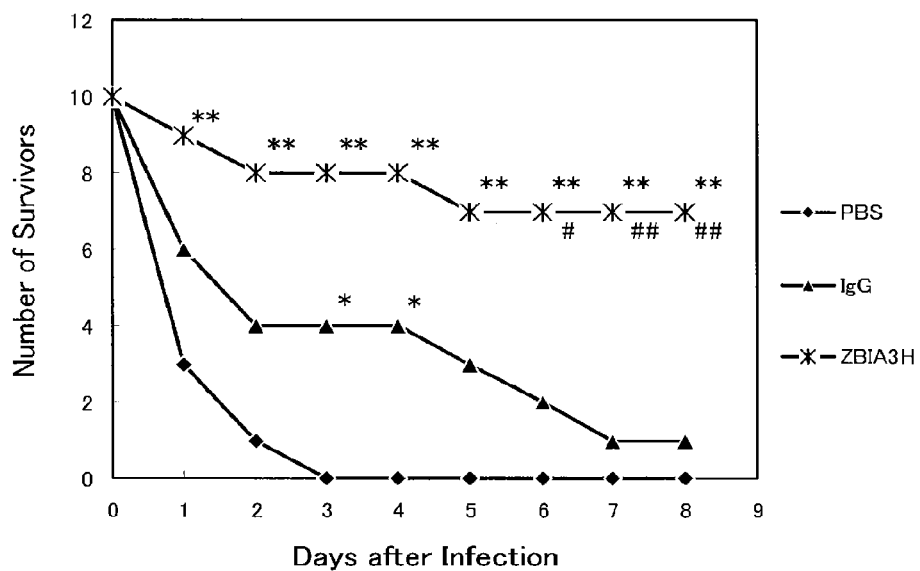
Effect of ZBIA3H Antibody in a Strain MW2 Induced Mouse Sepsis Model

[FIG. 6]
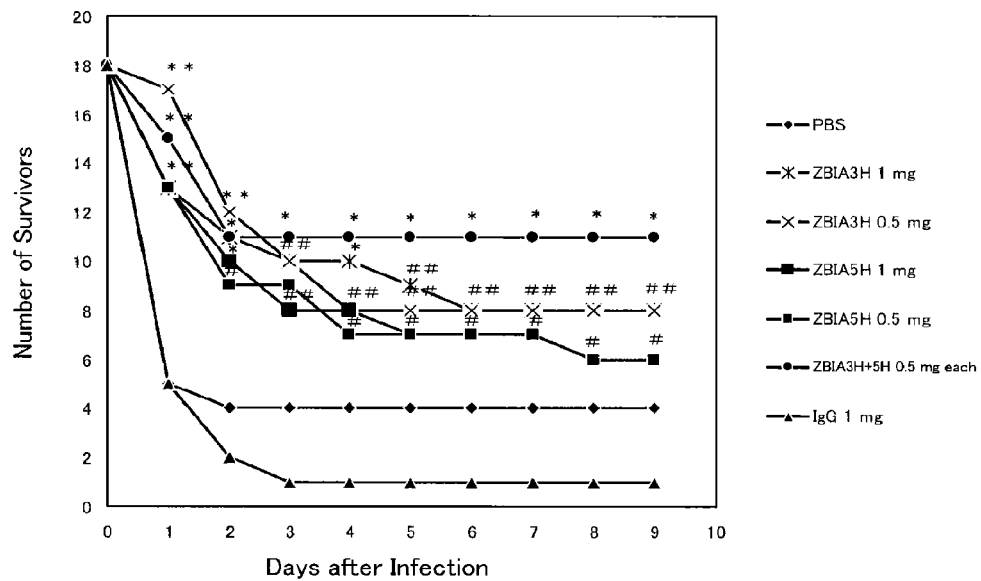
Effect of Combined Use of ZBIA5H Antibody and ZBIA3H Antibody on Strain MW2 Induced Sepsis
[FIG. 7]
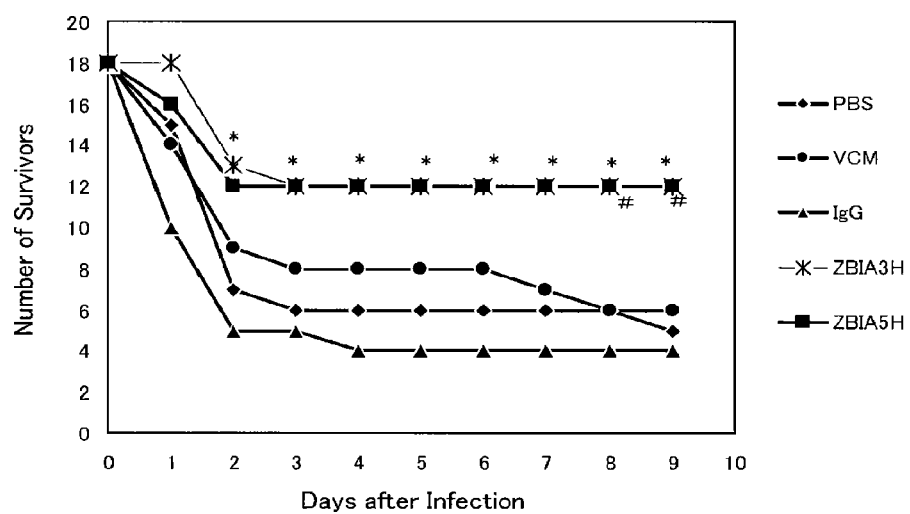
Effects of ZBIA5H Antibody and ZBIA3H Antibody in a Strain VRS1 Induced Mouse Sepsis Model

[FIG. 8]
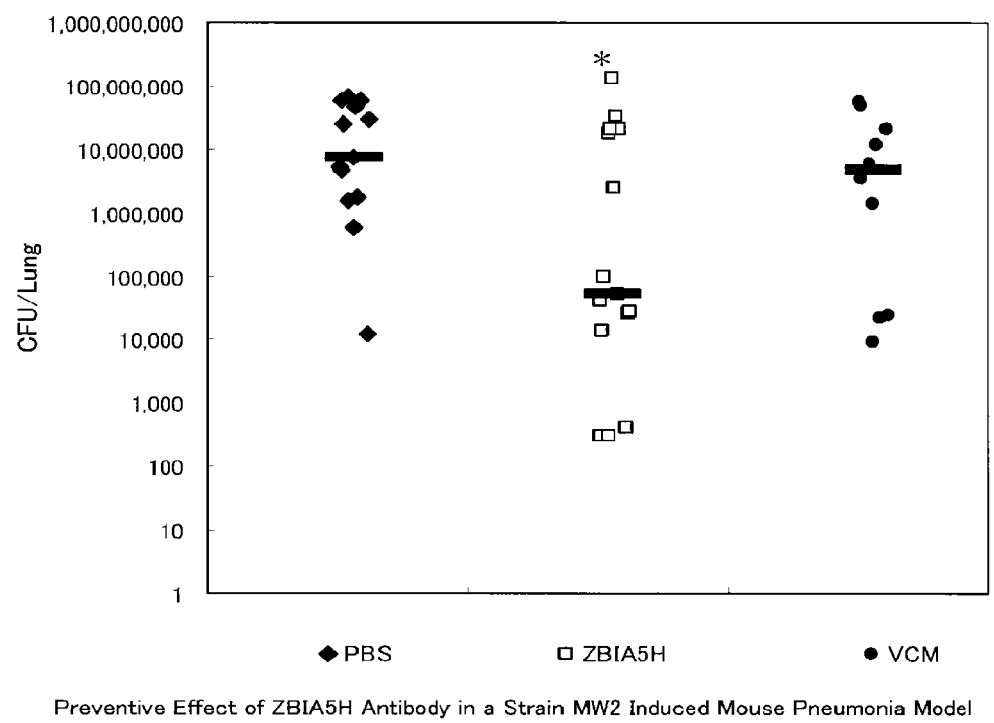
Preventive Effect of ZBIA5H Antibody in a Strain MW2 Induced Mouse Pneumonia Model

[FIG. 9]
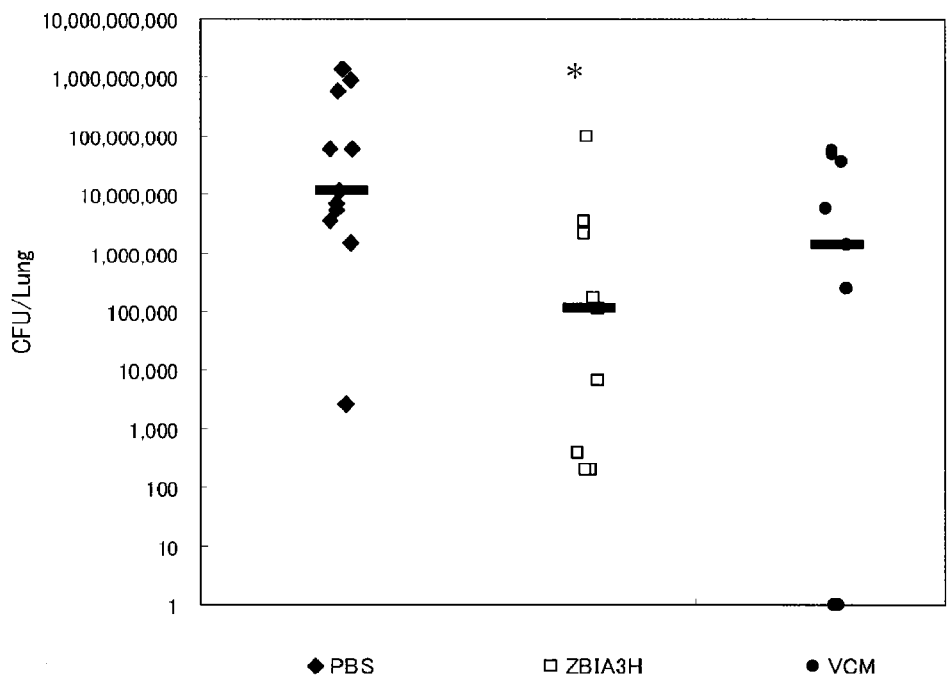
Preventive Effect of ZBIA3H Antibody in a Strain MW2 Induced Mouse Pneumonia Model
[FIG. 10]
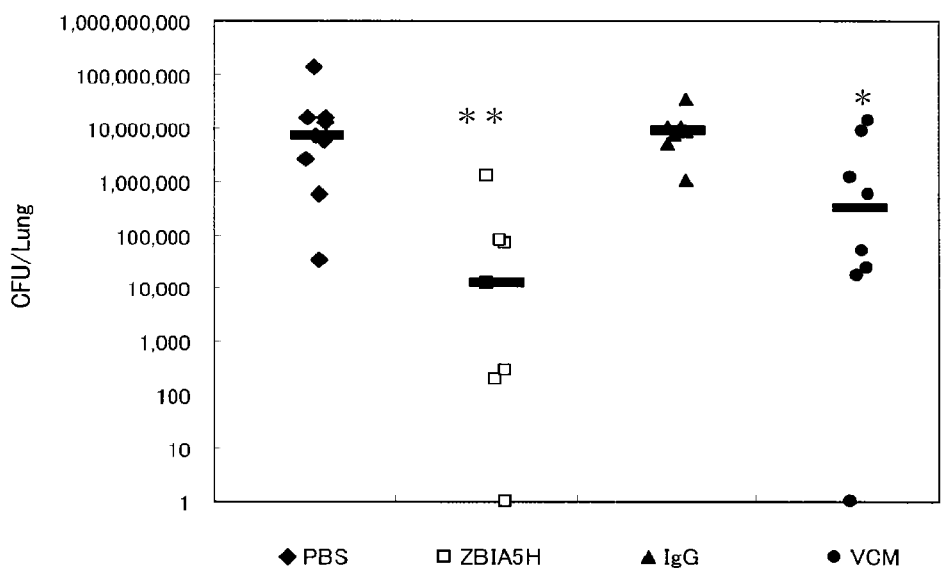
Therapeutic Effect of ZBIA5H Antibody in a Strain MW2 Induced Mouse Pneumonia Model

[FIG. 11]

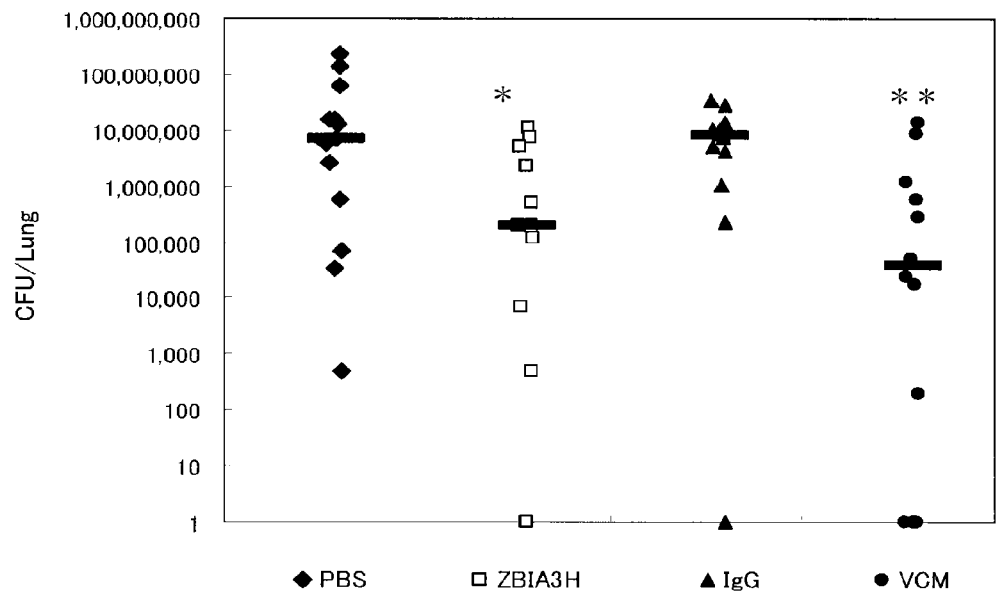

Therapeutic Effect of ZBIA3H Antibody in a Strain MW2 Induced Mouse Pneumonia Model

[FIG. 12]

```
ZBIA5H  VH
1:    QIQLVQSGPELKKPGETVKISCKASGYTFTDYSMHWVKQAPGKGLKWMGWINTETGEPTY    60
61:   ADDFKGRFAFSLETSASTAYLQINNLKNEDTATYFCARPYYAMDYWGQGTSVTVSS       116

ZBIA5H  VL
1:    DIQMTQSPSSLSASLGGKVTITCKASQDINKYIAWYQHKPGKGPRLLIHYTSTLQPGIPS   60
61:   RFSGSGSGRDYSFSISNLEPEDIATYYCLQYDNLLPWTFGGGTKLEIK              108
```

[FIG. 13]

```
ZBIA3H  VH
1:    EVQLVESGGGLVQPKGSLKLSCAASGFTFNTYAMNWVRQAPGKGLEWVARIRSKSNNYAT    60
61:   YYADSVKDRFTISRDDSQSMLYLQMNSLKTEDTAMYYCVRRGGNAIYYAMDYWGQGTSVT   120
121:  VSS                                                            123

ZBIA3H  VL
1:    QIVLTQSPAIMSASPGEKVTMTCSANSSVSYMHWYQQKSGTSPKAWIYDTSKLASGVPAR   60
61:   FSGSGSGTSYSLTISSMEAEDAATYYCQQWSSNPPTFGSGTKLEIK                106
```

ANTI-*STAPHYLOCOCCUS* ANTIBODY, METHOD FOR MANUFACTURING SAME, AND USAGE OF SAME

TECHNICAL FIELD

The present invention relates to antibodies that bind to *Staphylococcus*, production methods thereof, and uses thereof for staphylococcal infections.

BACKGROUND ART

Staphylococci are a type of indigenous bacteria in humans, and are also known to cause infections. For example, *Staphylococcus aureus* is said to be carried by 20-30% of people persistently, and by 50-60% of people transiently (Non-Patent Document 1). Other than in food poisoning, skin/soft tissue infections (such as impetigo and cellulitis) and the like, the bacteria are usually almost non-virulent to healthy individuals. However, they often cause serious infections in people such as patients who underwent highly invasive surgery, hemodialysis patients, patients who received bio-replacement with artificial medical devices, diabetic patients, and extremely premature infants whose immune systems are immature and in whom indigenous bacterial flora have not been formed.

The development of anti-microbial agents for staphylococci started with the β-lactam penicillin. However, staphylococci easily acquired a drug-resistance mechanism genetically, and resistant bacteria appeared a few years after penicillin went on sale. Various antimicrobial agents, such as aminoglycoside, macrolide, chloramphenicol, tetracycline, quinolone, and penem antimicrobial agents were subsequently developed, but were not able to overcome resistant bacteria. Additionally, bacteria resistant to vancomycin, a glycopeptide antimicrobial agent which did not have resistant bacteria for a long time after development, eventually appeared (Non-Patent Document 2). Furthermore, an oxazolidine antimicrobial agent, which was developed recently as the first novel antimicrobial agent in a few decades, was found to have resistant bacteria thereto the year it went on sale (Non-Patent Document 3).

As described above, multidrug-resistant staphylococci exhibiting resistance to most antimicrobial agents have emerged, and among them, *Staphylococcus aureus*, as the main pathogen of nosocomial infections, especially, imposes a great threat. In fact, it is estimated that the number of patients invasively infected by methicillin-resistant *Staphylococcus aureus* (MRSA) comes up to 94,000 in the USA annually, of whom, an estimated 18,000 die (Non-Patent Document 4). Moreover, with advanced medical care becoming available in countries outside of medically advanced countries, the chance and risk of contracting *Staphylococcus aureus* infections have become higher, and patients suffering from *Staphylococcus aureus* infections are predicted to increase in the future. Furthermore, cases of highly virulent community-acquired MRSA infections, where healthy individuals contract the infections in communities and exhibit severe symptoms, (Non-Patent Document 5) are also increasing.

Accordingly, new therapeutic strategies different from the conventional treatments with antimicrobial substances are strongly desired, and recently, studies have been carried out on infection protection using vaccines or antibodies. Examples of the vaccines include *Staphylococcus aureus* capsular polysaccharide types 5 and 8, and iron surface determinant B; and examples of the antibodies include antibodies for clumping factor A, ABC transporter, or teichoic acid.

Additionally, the disclosures of the following non-patent documents are all incorporated herein by reference.

Non-Patent Document 1: Rebecca A. Brady, Jeff G. Leid, Anne K. Camper, J. William Costerton, and Mark E. Shirtliff (2006) *Infect. Immun.* 74: 3415-3426.

Non-Patent Document 2: CDC (2002) *MMWR* 51: 565-567.

Non-Patent Document 3: Sotirios Tsiodras, Howard S. Gold, George Sakoulas, George M. Eliopoulos, Christine Wennersten, Lata Venkataraman, Robert C. Moellering Jr, and Mary Jane Ferraro (2001) *Lancet* 358: 207-208.

Non-Patent Document 4: R. Monina Klevens, Melissa A. Morrison, Joelle Nadle, Susan Petit, Ken Gershman, Susan Ray, Lee H. Harrison, Ruth Lynfield, Ghinwa Dumyati, John M. Townes, Allen S. Craig, Elizabeth R. Zell, Gregory E. Fosheim, Linda K. McDougal, Roberta B. Carey, and Scott K. Fridkin (2007) *JAMA* 298: 1763-1771.

Non-Patent Document 5: CDC. (1999) *MMWR* 48: 707-710.

Non-Patent Document 6: Adam C. Schaffer and Jean C. Lee (2009) *Infect. Dis. Clin. North. Am.* 23: 153-171.

SUMMARY OF THE INVENTION

Many of the conventional vaccines and antibodies for infection control do not provide adequate effects in clinical trials or pre-clinical trials (Non-Patent Document 6). The inadequate clinical effects of these vaccines or antibodies, which have specific capsular components, specific produced toxins, specific cell wall-binding proteins, or bacterial components as antigens, show the difficulties in obtaining an antibody that recognizes an appropriate epitope by conventionally practiced immunization methods.

The present inventors performed diligent studies in order to solve these problems, and succeeded in producing novel antibodies by using a *Staphylococcus* with the cell surface substances deacetylated as an antigen. Furthermore, the inventors succeeded in discovering specific antibodies that are effective in staphylococcal infection models.

The present invention provides an anti-*Staphylococcus* antibody that has a therapeutic or preventive effect on a staphylococcal infection, especially an anti-*Staphylococcus aureus* antibody. This antibody preferably can be obtained by immunization with a deacetylated *Staphylococcus*.

Moreover, the present invention provides an anti-*Staphylococcus* antibody comprising a complementarity determining region(s) (CDR(s)) derived from a ZBIA5H antibody or a ZBIA3H antibody (a ZBIA5H series antibody or a ZBIA3H series antibody). This antibody preferably comprises the same CDR(s) as the ZBIA5H antibody or ZBIA3H antibody.

Additionally, the present invention provides an anti-*Staphylococcus* antibody comprising a heavy chain variable region that comprises CDRH1, 2, and 3 respectively comprising amino acid sequences shown in SEQ ID NOs: 1, 2, and 3 or amino acid sequences shown in SEQ ID NOs: 9, 10, and 11; and a light chain variable region that comprises CDRL1, 2, and 3 respectively comprising amino acid sequences shown in SEQ ID NOs: 4, 5, and 6 or amino acid sequences shown in SEQ ID NOs: 12, 13, and 14.

Also, the present invention provides an anti-*Staphylococcus* antibody comprising a heavy chain variable region that comprises an amino acid sequence shown in SEQ ID NO: 7, and a light chain variable region that comprises an amino acid sequence shown in SEQ ID NO: 8 (a ZBIA5H series antibody).

In addition, the present invention provides an anti-*Staphylococcus* antibody comprising a heavy chain variable region that comprises an amino acid sequence shown in SEQ ID NO: 15, and a light chain variable region that comprises an amino acid sequence shown in SEQ ID NO: 16 (a ZBIA3H series antibody).

Moreover, the present invention provides an antibody produced by a hybridoma deposited under Accession Number: NITE BP-1367 or Accession Number:NITE BP-1366.

These antibodies are preferably capable of binding to *Staphylococcus aureus*.

Additionally, these antibodies are preferably capable of binding to other *Staphylococcus* (such as *Staphylococcus epidermidis, Staphylococcus saprophyticus* or *Staphylococcus haemolyticus*), especially preferably *Staphylococcus epidermidis*.

These antibodies preferably have a therapeutic or preventive effect on a staphylococcal infection, more preferably a therapeutic or preventive effect on a drug-resistant staphylococcal infection.

Furthermore, the present invention provides the anti-*Staphylococcus* antibody conjugated to an antimicrobial agent.

Moreover, the present invention provides a nucleic acid encoding the anti-*Staphylococcus* antibody, a vector comprising the nucleic acid, and a host cell comprising the vector.

Additionally, the present invention provides a method for producing the anti-*Staphylococcus* antibody, comprising culturing the host cell under conditions wherein the nucleic acid encoding the antibody expresses the antibody.

Furthermore, the present invention provides a composition comprising the anti-*Staphylococcus* antibody.

Moreover, the present invention provides a medicament for treating or preventing a staphylococcal infection, comprising the anti-*Staphylococcus* antibody.

Also, the present invention provides a method for treating or preventing a staphylococcal infection, comprising administering the anti-*Staphylococcus* antibody or the composition to a subject for whom the infection is to be treated or prevented.

In addition, the present invention provides use of the anti-*Staphylococcus* antibody or the composition in the manufacture of a medicament for treating or preventing a staphylococcal infection.

Additionally, the present invention provides the anti-*Staphylococcus* antibody or the composition for treating or preventing a staphylococcal infection.

Moreover, the present invention provides combined use of a ZBIA5H series antibody and a separate anti-*Staphylococcus* antibody, and a composition comprising both antibodies. The separate anti-*Staphylococcus* antibody is preferably a ZBIA3H series antibody.

Furthermore, the present invention provides an article of manufacture comprising: (a) a container; (b) a package insert and/or a label on the container; and (c) a composition comprising an anti-*Staphylococcus* antibody held in the container; wherein at least one of the package insert and/or the label on the container indicates that the composition can be used to treat or prevent a staphylococcal infection.

In addition, the present invention provides a method for producing an anti-*Staphylococcus* antibody, comprising immunizing a mammal with a deacetylated *Staphylococcus*, and obtaining an antibody-producing cell from the mammal.

Based on this method, various antigenicities can be offered by *Staphylococcus* deacetylation, and many types of novel antibodies can be produced.

Moreover, in the above embodiment, while not limited thereto, *Staphylococcus aureus* may be typically given as a clinically important *Staphylococcus* that causes infections.

BRIEF DESCRIPTION OF THE DRAWINGS

FIG. 1 shows the antibody titers for *Staphylococcus aureus* in the sera of mice immunized with a deacetylated *Staphylococcus*.

FIG. 2 shows the reactivity of an anti-*Staphylococcus* antibody in a *Staphylococcus aureus* solid phase Cell-ELISA.

FIG. 3 shows the reactivity of the ZBIA5H antibody and the ZBIA3H antibody in a *Staphylococcus epidermidis* solid phase Cell-ELISA.

FIG. 4 shows the effectiveness of the ZBIA5H antibody in a *Staphylococcus aureus* strain MW2 mouse sepsis model. The asterisk (*) represents a significant difference in the number of survivors to the PBS-administered group (Fisher's exact test) (*: P<0.05; **: P<0.01). The number sign (#) represents a significant difference in the number of survivors to the control IgG-administered group (Fisher's exact test) (#: P<0.05).

FIG. 5 shows the effectiveness of the ZBIA3H antibody in a *Staphylococcus aureus* strain MW2 mouse sepsis model. The asterisk (*) represents a significant difference in the number of survivors to the PBS-administered group (Fisher's exact test) (*: P<0.05; **: P<0.01). The number sign (#) represents a significant difference in the number of survivors to the control IgG-administered group (Fisher's exact test) (#: P<0.05; ##: P<0.01).

FIG. 6 shows the effectiveness of using the ZBIA5H antibody and the ZBIA3H antibody in combination in a *Staphylococcus aureus* strain MW2 mouse sepsis model. The asterisk (*) represents a significant difference in the number of survivors to the PBS-administered group (Fisher's exact test) (*: P<0.05; **: P<0.01). The number sign (#) represents a significant difference in the number of survivors to the control IgG-administered group (Fisher's exact test) (#: P<0.05; ##: P<0.01).

FIG. 7 shows the effectiveness of the ZBIA5H and ZBIA3H antibodies in a *Staphylococcus aureus* strain VRS1 mouse sepsis model. The asterisk (*) represents a significant difference in the number of survivors to the PBS-administered group (Fisher's exact test) (*: P<0.05). The number sign (#) represents a significant difference in the number of survivors to the VCM-administered group (Fisher's exact test) (#: P<0.05).

FIG. 8 shows the preventive effect of the ZBIA5H antibody in a *Staphylococcus aureus* strain MW2 mouse pneumonia model. The horizontal line (-) represents a median of the number of lung infecting bacteria. The asterisk (*) represents a significant difference in the number of infecting bacteria to the PBS-administered group (Wilcoxon rank sum test) (*: P<0.05).

FIG. 9 shows the preventive effect of the ZBIA3H antibody in a *Staphylococcus aureus* strain MW2 mouse pneumonia model. The horizontal line (-) represents a median of the number of lung infecting bacteria. The asterisk (*) represents a significant difference in the number of infecting bacteria to the PBS-administered group (Wilcoxon rank sum test) (*: P<0.05).

FIG. 10 shows the therapeutic effect of the ZBIA5H antibody in a *Staphylococcus aureus* strain MW2 mouse pneumonia model. The horizontal line (-) represents a median of the number of lung infecting bacteria. The asterisk (*) represents a significant difference in the number of infecting bacteria to the PBS-administered group (Wilcoxon rank sum test) (*: P<0.05; **: P<0.01).

FIG. 11 shows the therapeutic effect of the ZBIA3H antibody in a *Staphylococcus aureus* strain MW2 mouse pneumonia model. The horizontal line (-) represents a median of the number of lung infecting bacteria. The asterisk (*) represents a significant difference in the number of infecting bacteria to the PBS-administered group (Wilcoxon rank sum test) (*: P<0.05; **: P<0.01).

FIG. 12 shows the amino acid sequences of the variable regions (SEQ ID NOs: 7 and 8) of the ZBIA5H antibody. The underlined portions are the complementarily determining regions (CDRs) according to the Kabat definition.

FIG. 13 shows the amino acid sequences of the variable regions (SEQ ID NOs: 15 and 16) of the ZBIA3H antibody. The underlined portions are the complementarity determining regions (CDRs) according to the Kabat definition.

MODES FOR CARRYING OUT THE INVENTION

[Explanation of Terminology and Embodiments]

In the present specification, the following terms have the meanings indicated below, and each term represents each embodiment indicated below.

"*Staphylococcus*" refers to a Gram-positive coccus belonging to the *Staphylococcus* genus. A *Staphylococcus* can be identified/distinguished according to conventional methods based on its biochemical characteristics (for example, glucose fermentability and coagulase activity) or genetic characteristics. While not limited thereto, examples of *Staphylococcus* species include *Staphylococcus aureus, Staphylococcus epidermidis, Staphylococcus saprophyticus* and *Staphylococcus haemolyticus.*

Among *Staphylococcus* species, *Staphylococcus aureus* may be given as a clinically important, infection-causing species for which the present invention is particularly effective.

"*Staphylococcus aureus*" refers to a Gram-positive coccus belonging to the *Staphylococcus aureus* species. *Staphylococcus aureus* can be identified/distinguished according to conventional methods based on its biochemical characteristics (for example, glucose fermentability, coagulase activity and pigment producing ability) or genetic characteristics. While not limited thereto, examples of specific strains of *Staphylococcus aureus* include the MW2 strain, the USA300 strain, the Mu3 strain, the Mu50 strain, the COL strain, the N315 strain, and the VRS1 strain.

"*Staphylococcus epidermidis*" refers to a Gram-positive coccus belonging to the *Staphylococcus epidermidis* species, "*Staphylococcus saprophyticus*" refers to a Gram-positive coccus belonging to the *Staphylococcus saprophyticus* species, and "*Staphylococcus haemolyticus*" refers to a Gram-positive coccus belonging to the *Staphylococcus haemolyticus* species. These staphylococci can be identified/distinguished according to conventional methods based on their biochemical characteristics or genetic characteristics.

"Drug-resistant staphylococci" refer to staphylococci that acquired resistance to drugs such as antimicrobial substances (such as the various β-lactam, aminoglycoside, macrolide, chloramphenicol, tetracycline, quinolone, penem, glycopeptide, and oxazolidine antimicrobial agents), and include staphylococci with low resistance and staphylococci with hetero-resistance for the above drugs. In particular, a *Staphylococcus* that has acquired resistance for a plurality of drugs is referred to as a multidrug-resistant *Staphylococcus.*

Additionally, "drug-resistant *Staphylococcus aureus*" includes methicillin-resistant *Staphylococcus aureus* (MRSA) and vancomycin-resistant *Staphylococcus aureus* (VRSA). While not limited thereto, examples of specific strains of methicillin-resistant *Staphylococcus aureus* include the strain MW2 and the strain N315. As for vancomycin-resistant *Staphylococcus aureus*, while not limited thereto, an example includes the strain VRS1.

A "staphylococcal infection" refers to an infection caused by *Staphylococcus*.

While not limited thereto, infections caused by *Staphylococcus aureus* include food poisoning, skin/soft tissue infections (for example, acne, impetigo, folliculitis, furuncle, carbuncle, hidradenitis suppurativa, mastitis, infectious paronychia, cellulitis, pyomyositis, subcutaneous abscess, surgical site infection), bacteremia, sepsis, endocarditis, meningitis, brain abscess, osteomyelitis, arthritis, toxic shock syndrome, staphylococcal scalded skin syndrome, erythroderma secondary to infections, lymphadenitis, blepharitis, hordeolum, nongonococcal bacterial conjunctivitis, corneal ulcer, rhinitis, sinusitis, submandibular space infection, pharyngomaxillary abscess, purulent parotitis, pneumonia, lung abscess, pleural empyema, subphrenic abscess, intraabdominal abscess, pelvic abscess, retroperitoneal abscess, perinephric abscess, visceral abscess (splenic abscess, pancreatic abscess, hepatic abscess), anorectal abscess, prostatic abscess, prostatitis, urethritis, cystitis, and pyelonephritis, etc.

While not limited thereto, infections caused by *Staphylococcus epidermidis* include, especially where medical equipment, such as a catheter or a cardiac valve, is used, skin/soft tissue infections (for example, profound suppuration and chronic infection), bacteremia, sepsis, endocarditis, and osteomyelitis, etc.

While not limited thereto, infections caused by *Staphylococcus saprophyticus* include urinary tract infections, etc.

While not limited thereto, infections caused by *Staphylococcus haemolyticus* include urinary tract infections, etc.

At least some of the above infections tend to especially affect, in particular, patients with embedded artificial medical devices/implants (for example, artificial valves, artificial joints, central venous catheters, and cardiac valves), surgical patients, cancer patients, hemodialysis patients, premature infants, diabetic patients, immunocompromised patients, the elderly, and people using mechanical ventilators.

An "antibody" refers to an immunoglobulin polypeptide with an affinity for an antigen, and includes a full-length antibody and a portion thereof (fragment) having one pair or two pairs of polypeptide chains comprising a light chain and a heavy chain. Each heavy chain or light chain may include a variable region (associated with antigen recognition and binding) and a constant region (associated with localization and intercellular interactions). Most common full-length antibodies comprise two heavy chain constant regions ($C_H$), two heavy chain variable regions ($V_H$), two light chain constant regions ($C_L$), and two light chain variable regions ($V_L$). The variable region comprises complementarity determining regions (CDRs), which are sequences that confer antigen specificity on an antibody, and framework regions (FR).

Antibodies include monoclonal antibodies, polyclonal antibodies, multispecific antibodies formed from at least two antibodies (for example, bispecific antibodies), and antibody fragments having a desired biological activity. Moreover, antibodies include chimeric antibodies (for example, humanized antibodies), (complete) human antibodies, multivalent antibodies, and modified antibodies.

Additionally, an antibody may be of any class (for example, IgG, IgA, IgM, IgD, IgE) or any subclass so long as the effects of the invention are not compromised.

In addition, especially in cases where the antibody includes an Fc region, the antibody may comprise a sugar chain. Antibodies produced by mammalian cells typically include a branched oligosaccharide that is generally N-linked to Asn297 in the CH2 domain of the Fc region (for example, see Wright et al., (1997) *TIBTECH* 15: 26-32). Oligosaccharides may include various carbohydrates, for example, mannose, N-acetyl glucosamine (GlcNAc), galactose, and sialic acid, as well as fucose linked to GlcNAc in the "stem" of a biantennary oligosaccharide structure.

The "variable region" or "variable domain" refers to a domain that is present in the amino terminal region of a heavy chain or light chain of an antibody, and is generally the most variable in the antibody, and comprises an antigen binding site. The variable region in the heavy chain is referred to as $V_H$, and the variable region in the light chain is referred to as $V_L$. The variable region comprises three segments called complementarity determining regions (CDRs) or hypervariable regions (HVRs) that change at the highest frequency in the variable region, and segments called framework regions (FRs) that are relatively highly preserved. The heavy chain and light chain variable regions of a natural antibody each comprises three β-sheet structure-forming CDRs and four FR regions. The CDRs on each chain are linked to FRs, and together with the CDRs on the other chain, contribute to the formation of an antigen binding site on the antibody (for example, see Kabat et al., *Sequence of Proteins of Immunological Interest*, 5th Ed. National Institutes of Health, Bethesda, Md. (1991)).

A "complementarity determining region" or "CDR" (or "hypervariable region", "HVR" or "HV") refers to a region that is in the variable region of an antibody, is hypervariable, and forms a loop. In general, an antibody comprises three CDRs (CDRH1, CDRH2, CDRH3) in $V_H$, and three CDRs (CDRL1, CDRL2, CDRL3) in $V_L$.

Regarding the definition of CDR, any definition may be used so long as the effects of the invention are not compromised. While not limited thereto, CDR definitions that are usually used in the relevant technical field, such as Kabat, Chothia, AbM, and contact may be used as the CDR definition. The Kabat definition is based on sequence variation, and is the most commonly used (for example, see Kabat et al., *Sequences of Proteins of Immunological Interest*, 5th Ed. Public Health Service, National Institutes of Health, Bethesda, Md. (1991)). The Chothia definition also takes the location of structural loops into account (for example, see Chothia and Lesk *J. Mol. Biol.* 196: 901-917 (1987)). AbM is an intermediate definition between Kabat and Chothia's structural loops, and is based on the AbM antibody modelling software of Oxford Molecular Ltd. Contact is based on an analysis of complex crystal structures. The respective CDR definitions are shown below.

TABLE 1

| Loop | Kabat | Chothia | AbM | Contact |
|---|---|---|---|---|
| CDRL1 | L24-L34 | L26-L32 | L24-L34 | L30-L36 |
| CDRL2 | L50-L56 | L50-L52 | L50-L56 | L46-L55 |
| CDRL3 | L89-L97 | L91-L96 | L89-L97 | L89-L96 |
| CDRH1 | H31-H35B | H26- | H26- | H30- |

TABLE 1-continued

| Loop | Kabat | Chothia | AbM | Contact |
|---|---|---|---|---|
| (Kabat numbering) | | H32 ... 34 | H35B | H35B |
| CDRH1 (Chothia numbering) | H31-H35 | H26-H32 | H26-H35 | H30-H35 |
| CDRH2 | H50-H65 | H53-H55 | H50-H58 | H47-H58 |
| CDRH3 | H90-H102 | H96-H101 | H95-H102 | H93-H101 |

A CDR may comprise at least one of the following "extended CDRs":

$V_L$: 24-36 or 24-34 (CDRL1); 46-56 or 50-56 (CDRL2); 89-97 or 89-96 (CDRL3)

$V_H$: 26-35 (CDRH1); 50-65 or 49-65 (CDRH2); 93-102, 94-102 or 95-102 (CDRH3)

Unless clearly indicated, the amino acid residues in the light chain variable region or heavy chain variable region of an antibody are numbered using the "Kabat numbering system" (variable region residue numbering based on Kabat or Kabat's amino acid position numbering) in the present specification. In this numbering, an amino acid sequence may include an additional amino acid corresponding to an insertion in an FR or CDR in the variable region. For example, a heavy chain variable region may include amino acid insertions after the heavy chain FR residue 82 (such as residues 82a, 82b and 82c) and after CDRH2 residue 52 (residue 52a). The Kabat number of a residue can be determined by performing an alignment of homologous regions in antibody sequences based on a standard Kabat numbering sequence.

Moreover, when clearly indicated in particular, other numberings known to those skilled in the art, such as numbering based on Chothia, may also be used.

The "EU numbering system" or "EU index" is generally used when referring to a heavy chain constant region in an immunoglobulin. "Kabat's EU numbering" or "Kabat's EU index" is widely used in the numbering of human IgG1 or the like, based on a numbering system combining the above-described Kabat numbering and EU numbering. In the present specification, unless clearly indicated, residue numbering by the EU numbering system is used to number the amino acid residues in a constant region of an antibody.

A "constant region" or "constant domain" refers to a domain that is present in the carboxy terminal side of a heavy chain or light chain of an antibody, that generally has few changes, and that may be involved in localization or intercellular interactions (effector functions). The heavy chain constant region is referred to as $C_H$, and the light chain constant region is referred to as $C_L$.

An "Fc region" refers to a C-terminal region that is in the heavy chain of an antibody, and generally consists of CH2 and CH3 regions. While the boundary of an Fc region in the heavy chain may change, for example, the Fc region in human IgG heavy chain generally consists of from the amino acid residue of Cys226 or Pro230 to the carboxy terminus of the Fc region.

Based on the amino acid sequences of the constant regions in the heavy chains of antibodies, antibodies are assigned to different classes (for example, to five classes of IgA, IgD, IgE, IgG, and IgM; and further to subclasses (isotypes) such as $IgG_1$, $IgG_2$, $IgG_3$, $IgG_4$, $IgA_1$, and $IgA_2$). The heavy chain constant regions corresponding to the above-mentioned five classes are respectively called α, δ, ε, γ, and μ.

Moreover, the light chain of an antibody of a vertebrate species may take either kappa (κ) or lambda (λ) based on the amino acid sequence of its constant region.

The "effector function" of an antibody refers to a biological activity possessed by the Fc region of an antibody, and may change depending on the isotype of the antibody. Examples of effector functions of antibodies include C1q binding and complement-dependent cytotoxicity (CDC); Fc receptor binding; antibody-dependent cell-mediated cytotoxicity (ADCC); phagocytosis; impairment/inhibition of bacterial functions; toxin neutralization; and activation of immunocompetent cells (for example, B cells).

The above-mentioned Fc region usually provides binding sites for neutrophils, macrophages, other immunocompetent cells, complement complexes, and receptors in the immune system. When a bacterial protein (for example, protein A or protein G) binds to the Fc region in the vicinity of these binding sites, the normal function of the Fc region is inhibited, possibly interfering with the immune response against the bacteria. For example, protein A, which is a bacterial protein present on the cell wall of *Staphylococcus aureus*, can bind in the vicinity of the above binding sites in the Fc region of IgG. To avoid this, the Fc region can be changed so as not to bind to bacterial proteins (especially staphylococcal proteins). Such changes include, for example, amino acid addition, deletion, one or more amino acid substitutions, isotype (subclass) switch, and class switch in the amino acid sequence of an antibody.

Additionally, antibodies include modified antibodies that have been modified by any conventionally-known method. For example, sugar chain modifications (WO0061739, etc.) and amino acid mutations in the Fc region (US20050054832A1, now U.S. Pat. No. 7,317,091) and the like can increase binding to Fc receptors, etc., and provide better therapeutic effects.

A "monoclonal antibody" refers to an antibody obtained from a substantially uniform antibody group. The individual antibodies contained in the group, except for the few possibly existing mutations (for example, naturally-occurring mutations), are identical. Moreover, there is no particular preference regarding the monoclonal antibody production method, and monoclonal antibodies may be produced according to various conventional methods. Examples of their production methods include hybridoma method, recombinant DNA method (see, for example, U.S. Pat. No. 4,816,567 B), phage display technique, and techniques for generating human or human-like antibodies from an animal having genes encoding the entire or a part of a human immunoglobulin locus or a human immunoglobulin sequence.

A "chimeric antibody" refers to an antibody that has an amino acid sequence wherein the heavy chain or light chain or both are derived from a specific species, with the remaining portion consisting of an amino acid sequence derived from a different species. Examples include antibodies wherein the variable region, derived from an animal antibody such as a rat or mouse antibody, is fused to a separate molecule (for example, a constant region derived from a human antibody).

A "humanized antibody" is a type of chimeric antibody, wherein the variable region sequence of the heavy chain and/or light chain is changed so as to largely agree with a known human variable region sequence. Such changes are known in the conventional art, and while not limited thereto, are typically carried out by mutagenesis or CDR grafting. CDR grafting refers to the grafting of the CDRs of an antibody having the desired specificity to a human antibody framework, thereby exchanging the majority of the non-human sequence with a human sequence.

For example, according to the best fit method, the sequence of a variable region of a donor antibody is used to perform a screening on an entire library of known human variable region sequences, and the human sequence which is most similar to the donor sequence is used as the human framework of the humanized antibody. In a separate method, a specific framework obtained from a consensus sequence of all the human antibodies in a specific subgroup of the light chain or heavy chain is used. The same framework may be used for several different types of humanized antibodies.

An antibody is preferably humanized while preserving the affinity for an antigen and/or desired biological properties. As such, for example, three-dimensional models of the parent antibody sequence and humanized sequences may be used to carry out a process of analyzing the parent antibody sequence and various conceptual humanized products.

A humanized antibody may comprise a residue that is not found in the recipient antibody (human antibody) or the donor antibody (mouse antibody). By humanizing a mouse monoclonal antibody, the human anti-mouse antibody (HAMA) response is reduced.

A "human antibody" refers to an antibody wherein both the constant regions and variable regions of the heavy chain and light chain are all derived from human, or an antibody substantially identical thereto, and/or to an antibody produced using any of the techniques for producing human antibodies disclosed herein.

While human antibodies can be produced by various conventional art, the following method may be given as an example.

For example, a human antibody can be produced by combining an Fv clone variable region sequence, which is selected from a phage display library derived from human, with a known human constant region sequence.

Moreover, a human antibody may be prepared by administering an antigen to a transgenic animal (for example, a mouse; for example, an immunized XenoMouse) capable of producing a full repertoire of human antibodies without producing endogenous immunoglobulins in response to an antigen stimulation (for example, see U.S. Pat. Nos. 6,075, 181 B and 6,150,584 B relating to XenoMouse technology). Additionally, the homozygous deletion of an antibody heavy chain joining region (JH) gene in a germline mutant mouse is known not to produce endogenous antibodies. When these mice are grafted with an embryonic stem cell having a human germline immunoglobulin gene sequence, the administration of an antigen will result in the production of human antibodies in these mice.

In addition, human antibodies can be produced by the human B cell hybridoma technique (for example, see Li et al., *Proc. Natl. Acad. Sci. USA*, 103: 3557-3562 (2006)). The human myeloma and mouse-human heteromyeloma cell lines for producing human monoclonal antibodies are described in, for example, Kozbor, *J. Immunol.* 133, 3001 (1984); Brodeur et al., *Monoclonal Antibody Production Techniques and Applications*, pp. 51-63 (Marcel Dekker, Inc., New York, 1987); Boerner et al., *J. Immunol.*, 147: 86 (1991).

Moreover, where a human antibody has an affinity and properties similar to those of the non-human parent antibody (for example, a mouse antibody), gene shuffling may be used to obtain the human antibody from the non-human parent antibody (also called epitope imprinting; for example, see WO 93/06213). Different from the humanization of a non-human antibody by CDR grafting, this technique also allows the obtainment of human antibodies that do not have any FR or CDR residues of non-human origin.

An "antibody fragment" refers to a portion of an antibody comprising a variable region sequence sufficient to confer antigen binding. Such antibody portions, while not limited thereto, include Fab, Fab', F(ab')$_2$, Fv, scFv (single-chain antibodies), and diabodies. These antibody fragments may be produced according to conventional methods, and for example, may be produced by a proteolytic cleavage method such as papain digestion or pepsin digestion, or by a recombination method wherein the heavy chain and light chain cDNAs of an antibody are manipulated to generate heavy chain and light chain fragments separately or as portions in the same polypeptide. The papain treatment of an antibody generates two identical antibody fragments called "Fab" fragments, each having a single antigen binding site, and the remainder is named the "Fc" fragment, reflecting its ability to crystalize easily. The pepsin treatment of an antibody generates a "F(ab')$_2$" fragment, which has two antigen binding sites, and can cross-bind antigens.

Various techniques for producing antibody fragment have been developed. For example, these fragments can be induced by proteolysis (cleavage, digestion) of an antibody. Moreover, these fragments can be directly produced by recombinant host cells (for example, *E. coli* and phages). Additionally, an F(ab')$_2$ fragment can also be formed by chemically linking Fab'-SH fragments collected from host cells.

In an embodiment, the antibody is a single-chain Fv fragment (scFv). scFv is a species having a link site and lacking constant regions, and has the advantage of little non-specific binding in vivo. A scFv fusion protein may be configured to produce a fusion of an effector protein to the amino or carboxy terminus of scFv. In addition, the antibody fragment may be a "linear antibody," as described in, for example, U.S. Pat. No. 5,641,870 B. Such linear antibody fragments may be monospecific or bispecific.

An "Fv" fragment is the smallest antibody fragment comprising a complete antigen binding site. A double-chain Fv generally consists of a dimer of one heavy chain variable domain and one light chain variable domain. A single-chain Fv (scFv) generally has a peptide linker linking one heavy chain variable domain and one light chain variable domain by covalent bond. In these situations, the three CDRs in each variable region interact to form an antigen binding site on the dimer surface, and the six CDRs confer antigen binding specificity to the antibody. While a single variable region (or three CDRs specific to an antigen) has a lower affinity than the full binding site, it has the ability of recognizing and binding to the antigen.

A "Fab" fragment is an antibody fragment that comprises the light chain and heavy chain variable regions, and has the light chain constant region and the first constant region (CH1) of the heavy chain. A Fab' fragment is different from a Fab fragment in that the Fab' fragment has, in the carboxy terminus of the heavy chain CH1 region, several additional residues including one or more cysteines from the antibody hinge region. "Fab'-SH" refers to Fab' with a cysteine residue in the constant region carrying a free thiol group. Moreover, a "F(ab')$_2$" fragment is a pair of Fab' fragments having a disulfide bond formed by hinge cysteines between them.

A "diabody" refers to an antibody fragment with two antigen binding sites, and is formed by linking a heavy chain variable region (V$_H$) to a light chain variable region (V$_L$) in the same polypeptide chain (V$_H$-V$_L$). A short linker capable of pair formation of two domains on the same chain is used to force a domain and a complementary domain on a separate chain to form a pair, creating two antigen binding sites. A diabody may be bispecific. Similarly, a triabody and a tetrabody may be used.

A "multivalent antibody" refers to an antibody having three or more antigen binding sites. A multivalent antibody generally has a dimerization domain (for example, an Fc region or a hinge region) and three or more (for example, three to eight, especially four) antigen binding sites.

A "multispecific antibody" is an antibody (including an antibody fragment) having binding specificity for at least two different antigens, and in particular, an antibody (including an antibody fragment) having binding specificity for two different antigens is referred to as a "bispecific antibody."

"Binding affinity" refers to an overall strength of non-covalent interactions between a single binding site of a molecule (for example, an antibody) and its binding partner (for example, an antigen). Unless clearly indicated in particular, "binding affinity" refers to a binding affinity reflecting a 1:1 interaction between the members of a binding pair (for example, an antibody and an antigen). Affinity can be measured by methods known to those skilled in the art.

An antibody can be tested for its antigen binding activity by a known method, for example, ELISA or western blot.

An "anti-*Staphylococcus* antibody" or "*Staphylococcus* binding antibody" refers to an antibody capable of binding with an adequate affinity to a staphylococcal cell (live bacterium or dead bacterium) or to a molecule, which constitutes a *Staphylococcus* or is secreted by a *Staphylococcus* (protein, sugar, sugar chain, lipid), or a fragment thereof.

When the antibody is shown to have a binding affinity of at least 1.5-fold, at least 2-fold, at least 3-fold, at least 5-fold, or at least 10-fold, compared to non-specific binding (background), based on an assay such as ELISA, it may be said to bind specifically. More preferably, the binding of the antibody to other antigens (other bacteria or other organisms) compromising the effects of the present invention is at most 50%, at most 30%, at most 20%, at most 10%, at most 5%, at most 2%, or at most 1% of the binding to *Staphylococcus*.

Naturally, even in these situations, an antibody of the present invention may be an antibody that exhibits cross-binding to other antigens in a range allowing achievement of the purpose of the present invention, and such an antibody is also included in the antibodies of the present invention (for example, anti-*Staphylococcus aureus* antibodies may include not only antibodies that bind only to *Staphylococcus aureus*, but also antibodies that exhibit cross-binding to a different *Staphylococcus* (for example, *Staphylococcus epidermidis*, *Staphylococcus saprophyticus*, or *Staphylococcus haemolyticus*). Depending on the situation, the cross-reactivity is suitably used).

As an index of binding strength, for example, the dissociation constant (Kd) can be used, and to measure the binding strength, a method known in the field, such as ELISA, radioimmunoassay, or surface plasmon resonance can be used. Moreover, regarding the specific epitopes in these antigens, they can be identified using methods such as ELISA and western blot.

The antibodies also include antibodies conjugated to one or more drugs (especially antimicrobial substances) (in particular, such antibodies are sometimes called "antibody-drug conjugates" or "ADCs"). Moreover, the antibodies also include detectably labelled antibodies that are conjugated to one or more labeling markers (such as radioisotopes). Additionally, antibodies not conjugated to drugs or radiolabels are in particular called naked antibodies.

In such conjugated antibodies, an antibody (Ab) is conjugated to one or more drug moieties (D), preferably through a linker (L), for example, 1 to 20 drug moieties per antibody. Such conjugated antibodies can be produced by means using known organic chemical reactions and reagents. A conjugated antibody ($Ab-D_p$ or $Ab-(L-D)_p$), while not limited thereto, may be produced by, for example, (1) reacting the nucleophilic group of an antibody with a bivalent linker reagent to form Ab-L through a covalent bond, then reacting with a drug moiety; or (2) reacting the nucleophilic group of a drug moiety with a bivalent linker reagent to form D-L through a covalent bond, then reacting with the nucleophilic group of an antibody.

An "antimicrobial substance" is a substance having the function of inhibiting bacterial growth or killing bacteria. While not limited thereto, examples of antimicrobial substances include antibiotics, synthetic antimicrobial agents, lytic enzymes, and antimicrobial peptides.

Examples of "antibiotics" include penicillin, cefazolin, imipenem, gentamycin, tetracycline, chloramphenicol, erythromycin, daptomycin, and vancomycin.

Examples of "synthetic antimicrobial agents" include levofloxacin, moxifloxacin, and linezolid.

Examples of "lytic enzymes" include achromopeptidase, labiase, lysostaphin, lysozyme, and mutanolysin.

Examples of "antimicrobial peptides" include defensin, cathelicidin, hepcidin, histatin, lactoferrin, and dermcidin.

A "polynucleotide" or "nucleic acid" refers to a nucleotide polymer of any length, and includes DNA and RNA. Nucleotides include deoxyribonucleotides, ribonucleotides, modified nucleotides (for example, methylated nucleotides) or bases, and/or analogs thereof. Nucleotides are linked by DNA or RNA polymerase or by a synthetic reaction. A polynucleotide or nucleic acid may comprise a modification (for example, a link to a label or a protecting group) performed after linkage of the nucleotides. Moreover, an "oligonucleotide" refers to a short, generally single-chain polynucleotide. While not limited thereto, the term may refer to a synthetic polynucleotide of a length of less than 200 nucleotides in general.

A "vector" refers to a nucleic acid molecule capable of transferring other nucleic acids. Vectors include plasmids (circular double-stranded DNA linked to additional DNA(s)), phage vectors (phage linked to an additional polynucleotide), and virus vectors (viruses linked to an additional polynucleotide), etc. Certain vectors are capable of autonomous replication in host cells to which they are introduced (for example, bacterial vectors with a bacterial origin of replication and episomal mammalian vectors). Other vectors are incorporated into the host cell genome when introduced into host cells, and are replicated together with the host genome (for example, non-episomal mammalian vectors). Furthermore, certain vectors can direct the expression of genes operably linked thereto. Such vectors are called expression vectors or recombinant expression vectors. In general, expression vectors useful in recombinant DNA techniques often take the form of plasmids.

"Percent (%) amino acid sequence identity" and "percent (%) nucleotide sequence identity" are defined as the percentage of the number of amino acid residues that are identical between two amino acid sequences and the percentage of the number of bases that are identical between two nucleotide sequences, after aligning the sequences, introducing gaps where necessary to achieve maximum percent sequence identity, and not considering any conservative substitutions as part of sequence identity. Alignments for measuring % amino acid sequence identity and % nucleotide sequence identity can be achieved by using various methods within the range of skills of those skilled in the art, for example, publicly available computer software such as BLAST, BLAST-2, ALIGN, or Megalign (DNASTAR) software. Those skilled in the art would be able to determine appropriate parameters for the sequence alignment, including any algorithm necessary to achieve maximum length alignment on the full length sequences to be compared. For the purposes herein, % amino acid sequence identity values and To nucleotide sequence identity values are obtained by using the sequence comparison computer program BLAST.

A polypeptide or nucleic acid having a certain sequence identity may comprise several amino acid/nucleotide mutations (changes) with respect to the amino acid/nucleotide sequence that forms the basis. Such modifications are more preferable when they can improve the properties of the target molecule (for example, the binding affinity and/or biological properties of an antibody). An amino acid sequence mutant of a polypeptide may be prepared by introducing an appropriate nucleotide change in the nucleic acid of the polypeptide, or by peptide synthesis. Such a mutation includes deletion and/or insertion and/or substitution of a residue in the amino acid sequence. So long as the target molecule retains the desired characteristics, the deletion, insertion, and substitution may be combined in any manner.

Methods for introducing a mutation into a sequence, while not limited thereto, include isolation from a natural source (in the case of naturally occurring amino acid/nucleotide sequence mutants), site-specific mutation, PCR mutagenesis, and cassette mutagenesis.

A polypeptide may be modified to increase or decrease the level of glycosylation. The glycosylation of a polypeptide is typically either N-linked or O-linked. N-linked refers to the linkage of a carbohydrate moiety to the asparagine side chain. The tripeptide sequences, asparagine-X-serine, and asparagine-X-threonine (wherein X is any amino acid except for proline) are the recognition sequences for the enzymatic linkage of a sugar chain moiety to the asparagine side chain. Therefore, when any of the tripeptide sequences is present in a polypeptide, it becomes a potential glycosylation site. O-linked glycosylation refers to the linkage of N-acetylgalactosamine, galactose or xylose, to a hydroxy amino acid, most commonly serine or threonine, though sometimes the linkage occurs on 5-hydroxyproline or 5-hydroxylysine.

The addition or deletion of a glycosylation site on a polypeptide can be achieved by changing the amino acid sequence so as to produce or remove one or more of the above-mentioned tripeptide sequences (those of N-linked glycosylation sites). This change can also be carried out by adding, deleting, or substituting one or more serine or threonine residues on the polypeptide sequence that forms the basis (in the case of O-linked glycosylation sites).

Moreover, a polypeptide having a certain amino acid sequence may include cases where an oligosaccharide (sugar chain) linked to the polypeptide has been changed from a natural one.

Additionally, the preferred amino acid residue substitutions are conservative substitutions, and examples thereof are shown in Table 2. Such amino acid substitutions may be introduced into a polypeptide, and the substitution products may be screened for a desired activity/effect (for example, antigen binding, immunogenicity, ADCC, or CDC).

A non-conservative substitution is an exchange of a member in one of these classifications with one in a separate classification. So long as the desired characteristics are retained, non-conservative substitutions may also be performed.

TABLE 2

| Original residue | Exemplary substitution residue | Preferable substitution residue |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, norleucine | Leu |
| Leu (L) | norleucine, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Regarding antibody mutants, an amino acid residue in a complementarity determining region (CDR) and/or framework of the parent antibody may be changed. Methods for producing a mutant from a parent antibody, while not limited thereto, include affinity maturation (for example, by using phage display). Moreover, a mutant may be made by determining a candidate mutation site based on a crystal structure analysis of an antigen-antibody complex.

"Purification" refers to removal of impurities such that a target molecule is present in a sample at a concentration of at least 95%, at least 98%, or at least 99% by weight in the sample containing the molecule.

"Isolated" means that a target molecule is in a state of having been collected and/or separated from at least one other similar molecules (such as polypeptides or nucleic acids) that usually accompany the target molecule in a natural environment. Usually, an isolated molecule is prepared through at least one purification step.

"Mammals," while not limited thereto, include domestic animals (such as pigs, sheep, goats, horses, cattle (including beef cattle and dairy cattle), buffaloes, and camels), pet animals (such as cats and dogs), experimental animals (such as rabbits, mice, and rats), and primates (such as humans), etc.

"Treatment" refers to the reduction, alleviation, or palliation of an already-existing infection, and "prevention" refers to defense against future infections. The desired effects in a treatment include remission of symptoms, decrease of any direct or indirect pathological results of a disease, decrease in the speed at which symptoms worsen, recovery or alleviation of a disease state, and improvement of prognosis.

An "effective amount" refers to a drug dose capable of providing the desired effects when administered to a subject; a "therapeutically effective amount" refers to a drug dose capable of providing a therapeutic effect when administered to a subject; and a "preventively effective amount" refers to a drug dose capable of providing a preventive effect when administered to a subject. An effective amount can change depending on various factors, such as the activity, metabolic stability, reaction time, elimination rate, mode of delivery (method of administration), and administration time of each substance; the age, weight, general state of health, gender, and usual diet of the subject of treatment; combination of agents at the time of administration (drug interaction); and severity of the symptoms to be treated. Those skilled in the art can decide an effective amount in a conventional manner in view of the disclosures herein and information known in the relevant technical field. An effective amount can be administered as several separate doses per day (for example, two to four separate doses per day), or it can be administered as a single dose. Moreover, administration may be done on a daily, weekly, or monthly basis. Typically, a preventively effective amount is less than a therapeutically effective amount.

"Pharmaceutically acceptable" means not including other ingredients that are toxic and not tolerable to the subject to be administered, without markedly reducing the biological activity of an active ingredient.

"Aseptic" or "sterile" means antiseptic, or substantially not including any living microorganisms and spores thereof.

[Embodiments]

The present invention shall be explained below in detail using modes for carrying out the present invention, but the present invention is not limited thereby.

These embodiments may be taken alone, or a plurality of them may be combined. Additionally, see the above-mentioned "Explanation of Terminology and Embodiments" for the definition and details of each embodiment.

The well-known art and steps used in the present specification are sufficiently understood by those skilled in the art, and can be carried out according to conventional methods.

[Antibodies]

One embodiment of the present invention is an anti-*Staphylococcus* antibody that has a therapeutic or preventive effect (inhibitory effect on staphylococcal growth, *Staphylococcus*-damaging effect) on a staphylococcal infection, and is obtained by immunization with a deacetylated *Staphylococcus*.

Conventional antigen (epitope) selection did not always give sufficient results in vaccines/antibodies that have a capsular component, a specific toxin produced, a specific cell wall binding protein, a bacterial component, or the like as the antigen. As such, the present inventors, after diligent studies aiming to develop novel antigens and antibodies, discovered that antibodies made using a deacetylated *Staphylococcus* as the antigen exhibit superior effects in the treatment or prevention of staphylococcal infections, thus completing the present invention.

As the *Staphylococcus* in the above embodiment, while not limited thereto, the *Staphylococcus* cell itself may be used, and more preferably, the cell wall or a fraction/purified product or the like containing the cell wall may be used. As for the deacetylation method, while not limited thereto, enzymatic methods using a deacetylation enzyme, chemical methods using alkali treatment, and the like may be given. *Staphylococcus* treatment with ammonia water is simple and deacetylates under mild conditions, and is thus preferred. Details regarding the deacetylation method shall be described below.

The antibodies of the present invention can be suitably used to prevent/treat staphylococcal infections or to detect staphylococci. Among staphylococci, the antibodies of the present invention are particularly effective for *Staphylococcus aureus*. Additionally, the antibodies of the present invention can be suitably obtained by using *Staphylococcus aureus*, among staphylococci, as the antigen.

One embodiment of the present invention is an anti-*Staphylococcus* antibody comprising a CDR sequence(s)

derived from the ZBIA5H antibody or the ZBIA3H antibody. An anti-*Staphylococcus* antibody comprising a CDR(s) from the ZBIA5H antibody shall be called a ZBIA5H series antibody, and an anti-*Staphylococcus* antibody comprising a CDR(s) from the ZBIA3H antibody shall be called a ZBIA3H series antibody.

Since a CDR sequence is a sequence that confers antigen specificity to an antibody, so long as the antibody comprises a CDR sequence(s) from the ZBIA5H antibody or the ZBIA3H antibody, it would be able to exhibit the desired biological properties from the ZBIA5H antibody or the ZBIA3H antibody even when the other sequences are different.

CDRs derived from the ZBIA5H antibody or the ZBIA3H antibody are CDRs having amino acid sequences with at least 90%, at least 95%, at least 98%, or 100% amino acid sequence identity to the respective CDR sequences of the antibody. It is preferable to have a CDR identical to that of the ZBIA5H antibody or ZBIA3H antibody.

Regarding the CDRs in a variable region, their structures are kept by the framework regions, and together with the CDRs from the other chain, they contribute to the formation of an epitope on an antibody. Additionally, their amino acid sequences can be changed by known methods. CDRs having an amino acid sequence identity within a certain range are highly likely to have functionally equivalent antibody properties.

While a CDR may be based on any known definition so long as the effects of the present invention are not compromised, a CDR defined by Kabat, Chothia, AbM, or contact may be suitably used. A CDR defined by Kabat is more preferably used.

In other words, one embodiment of the present invention is an anti-*Staphylococcus* antibody wherein the heavy chain variable region comprises CDRs comprising amino acid sequences with at least 90%, at least 95%, at least 98%, or 100% amino acid sequence identity to the amino acid sequences shown in SEQ ID NOs: 1, 2, and 3 or the amino acid sequences shown in SEQ ID NOs: 9, 10, and 11; and the light chain variable region comprises CDRs comprising amino acid sequences with at least 90%, at least 95%, at least 98%, or 100% amino acid sequence identity to the amino acid sequences shown in SEQ ID NOs: 4, 5, and 6 or the amino acid sequences shown in SEQ ID NOs: 12, 13, and 14.

SEQ ID NO: 1 represents the heavy chain CDR1 in the ZBIA5H antibody, SEQ ID NO: 2 the heavy chain CDR2 in the ZBIA5H antibody, SEQ ID NO: 3 the heavy chain CDR3 in the ZBIA5H antibody, SEQ ID NO: 4 the light chain CDR1 in the ZBIA5H antibody, SEQ ID NO: 5 the light chain CDR2 in the ZBIA5H antibody, and SEQ ID NO: 6 the light chain CDR3 in the ZBIA5H antibody.

Additionally, SEQ ID NO: 9 represents the heavy chain CDR1 in the ZBIA3H antibody, SEQ ID NO: 10 the heavy chain CDR2 in the ZBIA3H antibody, SEQ ID NO: 11 the heavy chain CDR3 in the ZBIA3H antibody, SEQ ID NO: 12 the light chain CDR1 in the ZBIA3H antibody, SEQ ID NO: 13 the light chain CDR2 in the ZBIA3H antibody, and SEQ ID NO: 14 the light chain CDR3 in the ZBIA3H antibody.

Moreover, each of the above sequences is a CDR sequence defined by Kabat.

While not limited thereto, a representative example of a ZBIA5H series antibody is an anti-*Staphylococcus* antibody wherein the heavy chain variable region comprises CDRH1, 2, and 3 respectively comprising the amino acid sequences shown in SEQ ID NOs: 1, 2, and 3; and the light chain variable region comprises CDRL1, 2, and 3 respectively comprising the amino acid sequences shown in SEQ ID NOs: 4, 5, and 6.

Similarly, while not limited thereto, a representative example of a ZBIA3H series antibody is an anti-*Staphylococcus* antibody wherein the heavy chain variable region comprises CDRH1, 2, and 3 respectively comprising the amino acid sequences shown in SEQ ID NOs: 9, 10, and 11; and the light chain variable region comprises CDRL1, 2, and 3 respectively comprising the amino acid sequences shown in SEQ ID NOs: 12, 13, and 14.

An additional representative example of a ZBIA5H series antibody is an anti-*Staphylococcus* antibody comprising a heavy chain variable region that comprises an amino acid sequence with at least 90%, at least 95%, at least 98%, or 100% amino acid sequence identity to the amino acid sequence shown in SEQ ID NO: 7; and a light chain variable region that comprises an amino acid sequence with at least 90%, at least 95%, at least 98%, or 100% amino acid sequence identity to the amino acid sequence shown in SEQ ID NO: 8.

Similarly, an additional representative example of a ZBIA3H series antibody is an anti-*Staphylococcus* antibody comprising a heavy chain variable region that comprises an amino acid sequence with at least 90%, at least 95%, at least 98%, or 100% amino acid sequence identity to the amino acid sequence shown in SEQ ID NO: 15; and a light chain variable region that comprises an amino acid sequence with at least 90%, at least 95%, at least 98%, or 100% amino acid sequence identity to the amino acid sequence shown in SEQ ID NO: 16.

SEQ ID NOs: 7 and 8 are respectively heavy chain and light chain variable region sequences of the ZBIA5H antibody, and SEQ ID NOs: 15 and 16 are respectively heavy chain and light chain variable region sequences of the ZBIA3H antibody.

In these embodiments where the overall variable region sequences are defined, the therapeutic or preventive effects of the antibodies can be exhibited more certainly.

In one embodiment of the present invention, an antibody produced by a hybridoma deposited under Accession Number: NITE BP-1367 or Accession Number: NITE BP-1366 (respectively called the ZBIA5H antibody or ZBIA3H antibody) is provided.

The antibody of any one of the above embodiments is an antibody from an antibody obtained using a deacetylated *Staphylococcus* as the antigen.

In any one of the above embodiments, the antibody may be an antibody of any form so long as the effects of the present invention are not compromised.

These antibodies preferably have therapeutic or preventive effects on staphylococcal infections, and more preferably, have therapeutic or preventive effects on drug-resistant staphylococcal infections.

Moreover, the ZBIA5H series antibodies, when used in combination with a separate anti-*Staphylococcus* antibody (such as ZBIA3H series antibody), can provide even more prominent therapeutic or preventive effects on staphylococcal infections than when each is used alone.

In one embodiment, the above anti-*Staphylococcus* antibodies can bind to *Staphylococcus aureus*, and can also bind to *Staphylococcus epidermidis*, *Staphylococcus saprophyticus*, or *Staphylococcus haemolyticus*. Because of this cross-reactivity, they can be suitably used in the prevention, treatment, detection, or the like of not only *Staphylococcus aureus*, but also a separate *Staphylococcus*. In particular, they preferably exhibit a cross-reactivity with *Staphylococcus epidermidis*, an important *Staphylococcus* from the clinical standpoint.

An additional embodiment of the present invention is the antibody of any one of the above embodiments that is an antibody fragment or an antibody fragment from the antibody of any one of the above embodiments. The antibody fragment may be any of the above-mentioned antibody fragments so long as the effects of the invention are not compromised. The antibody fragment is preferably Fab or F(ab')$_2$. By being an antibody fragment, it excels in its productivity, and in migration/penetration into an infection focus.

An additional embodiment of the present invention is the antibody of any one of the above embodiments that is a chimeric antibody, a humanized antibody, or a human antibody; or a chimeric antibody, a humanized antibody, or a human antibody from the antibody of any one of the above embodiments. The chimeric antibody, humanized antibody, or human antibody may be any of the above-mentioned chimeric antibodies, humanized antibodies, or human antibodies so long as the effects of the invention are not compromised. By being a chimeric antibody, a humanized antibody, or a human antibody, it provides the effects of reducing antigenicity and improving in vivo kinetics.

An additional embodiment of the present invention is any one of the above antibodies conjugated to an antimicrobial substance. The antimicrobial substance may be any of the above-mentioned antimicrobial substances so long as the effects of the invention are not compromised. The antimicrobial substance is preferably an antibiotic, a synthetic antimicrobial agent, a lytic enzyme, or an antimicrobial peptide.

By being conjugated to an antimicrobial substance, it can provide further effects such as centralizing the effective antimicrobial substance to bacteria to thereby increase the antimicrobial effect of the antimicrobial substance, reducing side effects, and increasing the antimicrobial effect in cooperation with the effector effect of the antibody.

More preferably, the antibiotic is vancomycin. In this instance, side effects such as nephrotoxicity are reduced, and effects on vancomycin-resistant bacteria can also be provided.

More preferably, the synthetic antimicrobial agent is linezolid. In this instance, side effects such as cytopenia are reduced, and effects on linezolid-resistant bacteria can also be provided.

More preferably, the lytic enzyme is lysostaphin. In this instance, effects such as antigenicity reduction, in vivo kinetics improvement, bacteriolysis enhancement, and dose reduction can be provided.

More preferably, the antimicrobial peptide is cathelicidin. In this instance, effects such as antimicrobial effect enhancement and dose reduction can be provided.

[Screening and Production Methods]

One embodiment of the present invention is a screening method or a method for producing an anti-*Staphylococcus* antibody that has a therapeutic or preventive effect on a staphylococcal infection, comprising immunizing a mammal with a deacetylated *Staphylococcus*, and obtaining an antibody-producing cell from the mammal.

Based on this method, various antigenicities can be offered by *Staphylococcus* deacetylation, and many types of novel antibodies can be produced.

By *Staphylococcus* deacetylation, the present inventors surprisingly succeeded in obtaining epitopes that were unavailable until now due to conformational changes caused by deacetylation.

Histone may be given as an example where a change in the charge due to acetylation or deacetylation causes a change in the conformation or interaction of a substance. Histones are usually positively charged, and can electrostatically bind to negatively charged DNA. However, when acetylated by histone acetyltransferase, a histone loses its charge, and DNA binding weakens. Deacetylation by histone deacetylase makes the histone positively charged again, allowing it to bind to DNA easily.

A *Staphylococcus* also contains various acetyl-containing substances, and surprisingly, deacetylation of these substances enables obtainment of epitopes that were unavailable until now, and can add diversity to the antigen. As such, the method described in the present application is also suitable as a screening system for the obtainment of various novel antibodies.

Regarding the means for deacetylation, there are no limitations to the means so long as deacetylation is achieved, and examples thereof include enzymatic treatment and alkali treatment. Furthermore, means for deacetylating the N-acetyl muramic acid O-acetyl group on the cell wall of *Staphylococcus* are preferred.

As an example of such means, deacetylation using ammonia water may be given. Deacetylation using ammonia water can be performed by, for example, suspending staphylococci in ammonia water and stirring it.

The concentration of ammonia water is preferably 5 to 30% in view of the deacetylation and the non-specific denaturation effect, and more preferably 10 to 15% in view of the deacetylation reaction speed and the non-specific denaturation effect. The treatment temperature is preferably 4 to 50° C. in view of the deacetylation and the non-specific denaturation effect, and more preferably 30 to 40° C. in view of the deacetylation reaction speed and the non-specific denaturation effect. As for the treatment time, it is preferably 6 to 48 hours in view of the deacetylation and the non-specific denaturation effect, and more preferably 12 to 24 hours in view of the deacetylation reaction speed and the non-specific denaturation effect. Furthermore, stirring is preferred in the ammonia water treatment.

As for the *Staphylococcus*, so long as there is antigenicity, any part may be used, and the cell itself may be used. Preferably, a fragmented *Staphylococcus* is used, and a fraction containing much of the cell wall is more preferably used. A step of washing the fragmented *Staphylococcus* with a surfactant (Triton X-100) or distilled water, etc. may be included. The cell wall refers to a structure/capsule that is possessed by Plantae, Fungi, Archaea, and Bacteria other than mycoplasma, exists outside of the cell membrane (biomembrane separating the inside and outside of a cell) and surrounds a cell. The cell wall of Bacteria is mainly made of peptidoglycans, and the cell wall of Gram positive bacteria including staphylococci is made of peptidoglycans, cell wall teichoic acid, and cell wall binding proteins, etc. Regarding the cell wall, so long as the purpose of the present invention is achieved, a chemically synthesized component in a form having antigenicity may be used.

When using the cell wall, anything containing the target cell wall in a form having antigenicity may be used. Preferably, a fraction purified such as to contain the cell wall as the main ingredient can be preferably used. Methods for purifying the cell wall of Gram positive bacteria differ depending on the type or purity of the constituent material of the cells wall to be purified, and the acceptable level of denaturation. While not limited thereto, for example, 1) methods for obtaining a cell wall fraction by physically fragmenting a bacterium using a glass bead blender or ultrasound treatment, and centrifuging (for example, William Wiley Navarre, Hung Ton-That, Kym F. Faull, and Olaf Schneewind. 1998. Anchor structure of staphylococcal surface proteins II. COOH-terminal structure of muramidase and amidase-solubilized surface protein. *J. Biol. Chem.* 273, 29135-29142); or 2) methods for obtaining a cell wall constituent material by breaking down a bacterium chemically by boiling or using an acid, an enzyme or the like, and centrifuging or filtering (*Shin seikagaku jikken koza* 17 *Biseibutsu jikkenho* [New Lectures on Experiments in Biochemistry 17 Experimental Techniques for Microorganisms], The Japanese Biochemical Society, Ed., Tokyo Kagaku Dojin 1992) may be given.

In these screening and production methods, *Staphylococcus aureus* is suitably used as the *Staphylococcus*, and for example, the community-acquired *Staphylococcus aureus* strain MW2 that is regarded as a generally highly virulent strain, may be used as the *Staphylococcus aureus* strain.

The production method and screening method in any one of the above embodiments, while not limited thereto, may further include one or more of the steps or embodiments described in detail below.

(1) Immunization

An obtained antigen is administered to a mammal to perform immunization. The antigen may be used as a mixture with an adjuvant. As the mammal, a mouse is suitably used, and a BALB/c mouse is more suitably used. Immunization may be performed on the same mammal once or several times.

(2) Screening

A hybridoma is made using a conventional method from a splenocyte, and screening is performed using a desired activity, such as antibody titer, as an indicator. Before obtaining the splenocyte, a pre-screening on each immunized mammal may be performed using an activity in the serum, such as serum antibody titer, as an indicator. Moreover, the screening is preferably performed using ELISA, and more preferably using a *Staphylococcus* Cell-ELISA.

(3) Large Scale Preparation

A hybridoma selected by screening is administered to the peritoneal cavity of a mouse to induce ascites, and the antibody-containing ascitic fluid is collected and purified to obtain an anti-*Staphylococcus* antibody. Preferably, a SCID mouse is used as the mouse. For the purification, chromatography is preferably used, and affinity chromatography, for example, protein C affinity chromatography, is more preferably used.

(4) Recombination Production

For an antibody obtained by screening, the obtainment of a cDNA from a hybridoma producing the antibody allows a recombinant to be produced in other cells, and an embodiment like this is also included in the above production method.

The method for producing a recombinant in other cells using the obtained cDNA shall be described in detail below.

One embodiment of the present invention is a nucleic acid encoding the antibody of any one of the above embodiments. The nucleic acid is preferably DNA.

The nucleic acid of any one of the above embodiments can be isolated and sequenced by a conventional method. While not limited thereto, for example, an oligonucleotide primer designed to specifically amplify a heavy chain and/or a light chain or the like may be used for its sequencing.

Additionally, an isolated nucleic acid may be gene transferred into a prokaryotic or eukaryotic cell for cloning or expression.

Moreover, one embodiment of the present invention is a vector comprising the nucleic acid of any one of the above embodiments. Typically, the vector can be obtained by inserting the isolated nucleic acid of any one of the above embodiments into a vector by a conventional method. The vector is preferably a vector capable of replication, and more preferably a vector having an operatively linked promoter (expression vector). The vector, while not limited thereto, generally includes one or more components among a signal sequence, an origin of replication, one or more selector genes, a promoter, an enhancer element, and a terminator sequence.

Moreover, one embodiment of the present invention is a host cell comprising the vector of any one of the above embodiments.

A prokaryotic, yeast, or higher eukaryotic cell may be given as a suitable host cell. While not limited thereto, a bacterium (for example, a Gram negative or Gram positive bacterium) may be given as a suitable prokaryotic cell.

For polypeptide expression, a eukaryotic microorganism such as a filamentous fungus or yeast may also be suitably used.

Of higher eukaryotic cells, examples of invertebrate cells include plant and insect cells.

Additionally, a vertebrate cell is generally used as the host cell, and examples of useful mammalian host established cell lines include a monkey kidney CV1 cell line (COS-7, ATCC CRL1651) transformed with SV40; human embryonic kidney cell lines (HEK293 or HEK293 cells subcloned to grow in suspension culture); baby hamster kidney cells (BHK, ATCC CCL10); mouse Sertoli cells (TM4); monkey kidney cells (CV1, ATCC CCL70); African green monkey kidney cells (VERO-76, ATCC CRL-1587); human cervical cancer cells (HELA, ATCC CCL2); canine kidney cells (MDCK, ATCC CCL34); buffalo rat liver cells (BRL3A, ATCC CRL1442); human lung cells (W138, ATCC CCL75); human liver cells (HepG2, HB8065); mouse mammary tumor cells (MMT060562, ATCC CCL51); TRI cells; MRC5 cells; FS4 cells; and a human liver cancer cell line (HepG2). Other useful mammalian host cell lines include Chinese hamster ovary (CHO) cells including DHFR-CHO cells; and myeloma cell lines such as NS0 and Sp2/0.

Additionally, one embodiment of the present invention is a method for producing the antibody of any one of the above embodiments, comprising culturing the host cell of any one of the above embodiments under conditions wherein the nucleic acid expresses the antibody.

By transfecting the nucleic acid of any one of the above embodiments into a host cell that usually does not produce antibodies (for example, an *E. coli* cell, a monkey COS cell, a Chinese hamster ovary (CHO) cell, or a myeloma cell), inducing the promoter, and culturing in an appropriate nutrient medium, the antibody encoded by the nucleic acid can be produced. Subsequently, for example, the antibody can be produced by separating the antibody into a soluble fraction from a paste of the host cell and purifying (for example, by using a protein A or G column according to the isotype).

Host cells can be cultured in various media. Among commercially available media, for example, Ham's F10 (Sigma), MEM (Sigma), RPMI-1640 (Sigma) and DMEM (Sigma) are suitable for culturing host cells. These media may be supplemented, as necessary, with a hormone and/or another growth factor (for example, insulin, transferrin, or epidermal growth factor), a salt (for example, sodium, calcium or magnesium chloride, or a phosphate), a buffer (for example, HEPES), a nucleotide (for example, adenosine, or thymidine), an antibiotic (for example, gentamycin), a trace element (such as an inorganic compound usually present at a final concentration in the micromolar range), and glucose or an equivalent energy source. Other supplemental substances can also be included at appropriate concentrations known to those skilled in the art as necessary. Suitable culture conditions, such as temperature and pH, for each host cell are clear to those skilled in the art, or within the range of a simple consideration of conditions.

When using a recombination technique, the antibody is produced in the cell or the periplasmic space, or directly secreted into the medium.

When the antibody is produced in the cell, the first step is to remove unwanted substances (such as cell fragments) by, for example, centrifugation or ultrafiltration. Carter et al., *Bio/Technology* 10: 163-167 (1992) describes a method for isolating an antibody secreted in the periplasmic space of *E. coli*. In short, a frozen cell paste is thawed for about 30 minutes in the cold in the presence of sodium acetate (pH 3.5), EDTA and phenylmethylsulfonylfluoride (PMSF). The cell fragments can be removed by centrifugation.

When the antibody is secreted into the medium, the supernatant from the expression system is generally concentrated using a protein concentration filter (for example, an ultrafiltration filter from Amicon or Pellicon). A protease inhibitor such as PMSF may be included in any of the above steps to inhibit proteolysis, and an antibiotic may be used to prevent the growth of exogenous contaminating organisms.

An antibody composition prepared from a cell can be purified using, for example, hydroxyapatite chromatography, hydrophobic interaction chromatography, gel electrophoresis, dialysis, or affinity chromatography. Typically, affinity chromatography is the preferred technique for the purification step. The suitability of protein A/G as the affinity ligand depends on the species and isotype of the immunoglobulin Fc region present in the antibody. Protein A can be used to purify antibodies based on the human γ1, γ2, or γ4 heavy chain. Protein G can be suitably used for all mouse isotypes and all human γ heavy chains including human γ3. While the matrix to which the affinity ligand is bound is most often agarose, other materials can also be used. A mechanically stable matrix, such as controlled pore glass or poly(styrenedivinyl)benzene, allows a faster flow rate and a shorter processing time than those achievable using agarose. When the antibody includes a $C_H3$ domain, Bakerbond ABX resin (J.T. Baker, Phillipsburg, N.J.) is useful in the purification. Fractionation using an ion exchange column, ethanol precipitation, reverse phase HPLC, chromatography with silica, chromatography with heparin, sepharose chromatography on an anion or cation exchange resin (polyaspartic acid column), chromatofocusing, SDS-PAGE, and ammonium sulfate precipitation can also be used depending on the antibody to be collected.

Following the above-mentioned preliminary purification steps, a liquid mixture containing the target antibody and contaminants may be subjected to, for example, a low pH hydrophobic interaction chromatography using an elution buffer at a pH of about 2.5 to 4.5, and preferably with a low salt concentration (for example, about 0-0.25 M salt).

[Compositions]

An additional embodiment of the present invention is a composition comprising the antibody of any one of the above embodiments.

Yet an additional embodiment of the present invention is a composition comprising a ZBIA5H series antibody and a separate anti-*Staphylococcus* antibody. The separate anti-*Staphylococcus* antibody is preferably a ZBIA3H series antibody.

By using a ZBIA5H series antibody in combination with a separate anti-*Staphylococcus* antibody (for example, a ZBIA3H series antibody), an even better therapeutic or preventive effect can be provided on a staphylococcal infection than respective single administrations, so the composition of the above embodiment is particularly effective.

The composition of any one of the above embodiments is preferably a pharmaceutical composition (or medicament), and more preferably a pharmaceutical composition (or medicament) for treating or preventing a staphylococcal infection. Additionally, the composition preferably comprises a pharmaceutically acceptable carrier. Moreover, the composition may take any form of formulation. Further, when containing at least two active ingredients, the composition may be a combination/compound agent.

The composition of any one of the above embodiments may be in either a lyophilized form or a solution form, so long as the effects of the present invention are not compromised. Preferably, it is provided in a lyophilized form. In the case of a lyophilized product, it is dissolved in a pharmaceutically acceptable aqueous carrier (for example, sterile water for injection or sterile physiological saline) when used.

The pharmaceutically acceptable carrier may be a sterilized/aseptic liquid such as water or an oil (including petroleum, animal oils, plant oils, peanut oil, soy oil, mineral oils, sesame oil, and the like). Saline (especially physiological saline), an aqueous dextrose solution, and a glycerol solution can also be used as the liquid carriers (especially the liquid carriers for injection solutions). See *Remington's Pharmaceutical Sciences*, 18th Edition for suitable pharmaceutically acceptable carriers.

Further, the composition of any one of the above embodiments may include any kind of delivery medium and/or carrier. Such a medium can increase the half-life of an active ingredient when stored and administered (while not limited thereto, including applications to the skin, wounds, eyes, lungs, nasal mucosa, or gastrointestinal tract mucosa), or when inhaled into the nostrils or ventilated. While not limited thereto, carriers include natural polymers, semisynthetic polymers, synthetic polymers, liposomes, and semisolid formulations, etc. Examples of natural polymers include proteins and polysaccharides. Semisynthetic polymers are modified natural polymers, and include, for example, chitosan (a natural polysaccharide in the deacetylated form) and chitin. Synthetic polymers, include, for example, polyphosphoesters, polyethylene glycol, polylactic acid, polystyrene sulfonate, and poly(lactide-co-glycolide). Semisolid formulations include, for example, dendrimers, creams, ointments, gels, and lotions. Additionally, these carriers can be used in the microcapsulation of compositions, or may be covalently bonded to active ingredients (for example, antibodies).

The composition of any one of the above embodiments may be a composition for a use described below (for example, therapeutic use and/or preventive use of a staphylococcal infection).

Moreover, the composition of any one of the above embodiments may be a corresponding medicament.

Additionally, the composition of any one of the above embodiments includes cases where the antibody of any one of the above embodiments is used in combination with a separate agent or an anti-*Staphylococcus* antibody as described above or below, or where the two agents used in combination form a composition in situ.

[Articles of Manufacture]

An additional embodiment of the present invention is an article of manufacture, comprising (a) a container; (b) a package insert and/or a label on the container; and (c) a composition comprising the antibody of any one of the above embodiments or the composition of any one of the above embodiments, which is held in the container; wherein at least one of the package insert and/or the label on the container indicates that the composition can be used to treat or prevent a staphylococcal infection.

Suitable containers include, for example, bottles, vials, and syringes. The containers may be formed from various materials, for example, glass or plastic. The container may hold the composition and have a sterile access port (for example, the container may be a vial, or a bag of solution for intravenous administration, having a stopper that allows a hypodermic needle to pass through). The package insert and/or label indicates that the composition can be used to treat or prevent a staphylococcal infection. Furthermore, the article of manufacture may be an embodiment comprising (a) a first container that holds the composition; and (b) a second container that holds a separate composition (a separate composition included in any one of the above embodiments or a separate composition not included in any one of the above embodiments) or an agent or the like, and such an embodiment is also included in the article of manufacture of the present invention. In addition, the article of manufacture may further include a second or a third container containing a pharmaceutically acceptable buffer (while not limited thereto, for example, sterile distilled water for injection, sterile saline, phosphate buffered saline, Ringer's solution, or a dextrose solution). Additionally, it may include other configurations (while not included thereto, for example, a separate buffer, a diluent, a filter, a needle, and/or a syringe) that are desirable commercially or from the standpoint of users.

[Therapeutic/Preventive Methods and Medicaments]

An additional embodiment of the present invention is a method for treating or preventing a staphylococcal infection, comprising administering the antibody or composition of any one of the above embodiments to a subject for whom the infection is to be treated or prevented.

An additional embodiment of the present invention is a medicament for treating or preventing a staphylococcal infection, comprising the antibody or composition of any one of the above embodiments.

Moreover, an additional embodiment of the present invention is a use of the antibody or composition of any one of the above embodiments in the manufacture of a medicament for treating or preventing a staphylococcal infection.

Furthermore, an additional embodiment of the present invention is the antibody or composition of any one of the above embodiments for used in the treatment or prevention of a staphylococcal infection.

For the sake of simplicity, these embodiments shall be collectively referred to as the medicinal use embodiment.

According to the above medicinal use embodiment, therapeutic or preventive effects on a staphylococcal infection may be obtained. The subject for whom the treatment or prevention is to be performed, while not limited thereto, is preferably a mammal, more preferably a human being. Additionally, the subject to be treated is preferably a subject infected or suspected of being infected with a *Staphylococcus*. Regarding target staphylococcal infections, including those described above, while not limited thereto, a therapeutic or preventive effect may be provided preferably on bacteremia, sepsis, pneumonia, endocarditis, osteomyelitis, arthritis, meningitis, enteritis, purulent skin diseases, urinary tract infections, and medical device/implant-related infections; more preferably, on bacteremia, sepsis, and pneumonia. Target *Staphylococcus* species, including those described above, while not limited thereto, include *Staphylococcus aureus, Staphylococcus epidermidis, Staphylococcus saprophyticus*, and *Staphylococcus haemolyticus*; and *Staphylococcus aureus* is a particularly suitable target. Regarding target *Staphylococcus aureus* strains, including those described above, while not limited thereto, a therapeutic or preventive effect may be provided preferably on the strain USA100, the strain USA300, the strain COL, the strain HIP5827, the strain N315, the strain MW2, and the strain VRS1; more preferably on the strain MW2 and the strain VRS1.

Additionally, the above medicinal use embodiment can preferably provide effects on drug-resistant staphylococci. For example, while not limited thereto, since the medicinal use embodiment of the present invention can provide effects on methicillin-resistant staphylococci, it is expected to serve as an alternative medicament for when vancomycin administration is restricted (careful administration in patients with kidney diseases who are on hemodialysis). Furthermore, the embodiment can also provide therapeutic or preventive effects on vancomycin-resistant staphylococci.

Moreover, due to the fact that staphylococci are indigenous bacteria, conventional *Staphylococcus* vaccines was subject to improvement with respect to the difficulty in immunization, and in cases where the patient to be treated is immunodeficient (immunodeficiency is not rare among patients with staphylococcal infections), with respect to insufficient immunization. The above medicinal use embodiment improves these points, and may be more useful than conventional vaccines in at least one aspect.

Yet an additional embodiment of the present invention is a medicinal use embodiment of the above embodiment, wherein a ZBIA5H series antibody is used in combination with a separate anti-*Staphylococcus* antibody. The separate anti-*Staphylococcus* antibody, while not limited thereto, could be, for example, a ZBIA3H series antibody or an analog thereof.

Compared to use alone, a ZBIA5H series antibody can provide even better effects when used in combination with a separate anti-*Staphylococcus* antibody (especially a ZBIA3H series antibody or an analog thereof).

Regarding combined use, two antibodies may be administered simultaneously, or one antibody may be administered before or after the other; and two or more antibodies may be provided in a mode of formulation where they are either in the same formulation or in different formulations.

Regarding the active ingredient that can be used in combination with the present invention, while not limited to the above embodiment (a separate anti-*Staphylococcus* antibody), for example, an antimicrobial substance, a separate agent (for example, vancomycin, teicoplanin, arbekacin, linezolid, daptomycin, imipenem, norfloxacin, gentamycin), or an adjuvant may be used in combination.

In the above medicinal use embodiment, so long as the effects of the invention are not compromised, there is no limitation to the route of administration, and administration may be performed by, for example, intravenous, intraperitoneal, in vivo injection, intraarticular, intracerebroventricular, intraspinal, intramuscular or subcutaneous injection, or intranasal, dermal, intradermal, intracavitary, oral administration, or a separate effective administration method. Moreover, for example, topical administration to a specific infected area may be performed by intramuscular or subcutaneous injection. Furthermore, direct administration to a patient may be performed by swab application, immersion, soaking, or wiping. Moreover, applications may also be made to devices or apparatus embedded in the body, such as indwelling catheters, cardiac valves, cerebrospinal fluid shunts, joint prostheses and other implants, or other tools or devices at the danger of infection by Gram positive bacteria.

In the above medicinal use embodiment, after an agent of the present invention has been prepared, it is divided into one dose and administered. Factors that should be taken into consideration with respect to administration include the disease to be treated, the agent to be administered (antibody), the clinical condition of the subject to be administered (severity and progress, etc.), response of the subject to be administered to the agent, the medical/clinical history of the subject to be administered, the cause of the disease, the site to which the agent is to be delivered, method of administration, schedule of administration, whether the administration is for treatment or prevention, the decision of the physician in charge, and other factors. Moreover, when used in combination with a separate agent or the like, the effective amount of the other agent or the like can also vary depending on each of the above factors, in addition to the dose of the agent of the present invention. While not limited thereto, the above medicinal use embodiment is generally carried out at a dose and by a route of administration that are the same as those described below, or at any dose or by any route of administration that are empirically/clinically determined as appropriate.

An appropriate dosing regimen can be determined based on the knowledge in the art, the information provided in the present specification and experience regarding the individual subjects to be treated. Usually, in a medicinal use embodiment, an active ingredient (an antibody or the like) is preferably administered at a concentration that can provide effective results without causing dangerous or adverse side effects.

Typically, upon considering the above factors, an antibody at about 1 mg/kg to 1,000 mg/kg may be administered, for example, once or divided into two to three or more times, or as an initial candidate dose to be administered to a patient by continuous infusion. For administration to a blood vessel, though differing depending on the symptoms, age, weight of the patient, for example, a daily dose of 60 to 60,000 mg can be administered to an adult weighing 60 kg once or divided into two to three or more times. One typical daily dose, further depending on the above factors, is about 100 mg to 5,000 mg. Depending on the symptoms, repeated administration over several days or longer is usually continued until the desired suppression of the disease symptoms is achieved. Such a dose may be administered intermittently, for example, every three days, every week, or every three weeks. After an initial higher loading dose, one or more lower doses may be administered. In cases of intracavitary administrations, such as intrathoracic, intraperitoneal or intraspinal administrations, or administrations to local parts, such as intravesical administration, though differing depending on the symptoms of the patient, a daily dose of 10 mg to 5,000 mg can be administered once or divided into two to three or more times.

Typical administration examples have been shown above, but the present invention is not limited thereby.

The progress of these treatments can be easily monitored by regular diagnosis or assays.

In the above medicinal use embodiment, where an agent of the present invention is formulated at a fixed dose, an antibody or the like within the above dose range may be suitably used. Additionally, in the case of a combination formulation (combination/compound agent), the antibody or the like within the above dose range is used with a separate pharmaceutically active agent within an approved dose range. Where a combination formulation is not appropriate, the antibody or the like and the separate pharmaceutically active agent within the approved dose range may be used in succession.

Additionally, the administration of an anti-microbial drug alone is often insufficient in staphylococcal infections, so the agents of the present invention may be used in combination with a surgical intervention on the nidus (such as the changing of an artificial valve, removal of a catheter, or incision and drainage of an articular cavity) as necessary.

Moreover, *Staphylococcus aureus*, a clinically important *Staphylococcus*, can most typically be the target in any one of the above embodiments. Furthermore, when *Staphylococcus aureus* is chosen as the *Staphylococcus*, the present invention can more certainly provide its superior effects.

While modes for carrying out the present invention have been described above, they serve to illustrate the present invention, and various configurations other than the above may be used.

For example, in any one of the above embodiments, a ZBIA9H (series) antibody may be used instead of a ZBIA3H (series) antibody or in combination with a ZBIA3H (series) antibody. The ZBIA9H series antibody preferably comprises the same CDR(s) as the ZBIA9H antibody. For a ZBIA9H (series) antibody, the amino acid sequences of SEQ ID NOs: 17, 18, 19, 20, 21, 22, 23, and 24 are respectively used instead of the amino acid sequences of SEQ ID NOs: 9, 10, 11, 12, 13, 14, 15, and 16 in a ZBIA3H (series) antibody.

Furthermore, for example, while the above embodiments provided explanations centering on the medicinal use as therapeutic/preventive drugs for staphylococcal infections, they are not meant to limit the invention in particular. The present invention is expected to have a wide range of uses in addition to the medicinal use as therapeutic/preventive drugs for staphylococcal infections, such as diagnosis of staphylococcal infections, *Staphylococcus* detection, prevention of food poisoning caused by *Staphylococcus*, veterinary drugs and research reagents, and these uses are not intended to be excluded.

EXAMPLES

The present invention shall be explained using examples below, but these examples do not limit the present invention. Additionally, unless particularly indicated, the commercially available reagents mentioned in the examples were used according to the manufacturer's instructions or conventional methods.

Example 1

Preparation of Monoclonal Antibodies for *Staphylococcus*
Preparation of Immunizing Antigen The *Staphylococcus aureus* strain MW2 was cultured in Tryptic Soy Broth (BD; hereinafter "TSB") until the late logarithmic growth phase, collected by centrifugation, and then fragmented using a glass bead blender. After the fragmented cells were washed with Triton X-100 and distilled water, they were collected by centrifugation to obtain a purified cell wall product. To increase the immunogenicity and to make the production of various antibodies easier, the product was suspended in 12.5% ammonia water, and stirred for 16 hours at 37° C. to carry out a deacetylation treatment of the N-acetyl muramic acid O-acetyl group (deacetylated cell wall purified product: immunizing antigen).

Immunization

The immunizing antigen, at 2 mg/mL, 20 mg/mL and 200 mg/mL, was mixed with an equal volume of Freund's complete adjuvant (hereinafter "FCA") or Freund's incomplete adjuvant (hereinafter "FIA") to produce emulsions, and these were used as the immunogens.

When performing the initial immunization, 0.2 mL of the emulsions of the immunizing antigen and FCA were administered to the peritoneal cavity of each female BALB/c mouse (Charles River Laboratories Japan, Inc.) (amount of antigen administered 0.2 mg, 2 mg and 20 mg; 5 mice per group), and the emulsions with FIA were administered afterwards in a similar manner every two weeks until the fourth immunization.

Blood was collected from the tail vein a week before the initial immunization and a week after each immunization, and the antibody titers of anti-*Staphylococcus* antibodies in the serum were measured using *Staphylococcus aureus* solid phase cell-ELISA. The antibody titers rose with every additional immunization, and in general, mice administered with a higher amount of the antigen (the group administered with 20 mg of the antigen) had a higher antibody titer (FIG. 1, 20 mg—1, 2, 3, 4, 5).

Moreover, mouse 20 mg—2 was administered intravenously with 5 mg of the antigen as the final immunization.

*Staphylococcus aureus* Solid Phase Cell-ELISA

In order to detect antibodies actually capable of binding to an infectious *Staphylococcus* capable of growth, the binding of the anti-*Staphylococcus* antibodies was measured using *Staphylococcus aureus* solid phase Cell-ELISA in which live cells were immobilized onto a solid phase.

A protein A knock-out OS2 strain was grown in stationary culture for 16 hours at 30° C. in TSB, collected by centrifugation, washed three times using Dulbecco's phosphate buffered saline (-) (hereinafter "PBS"), and adjusted to a concentration of about $A_{600}$=0.1.

This was dispensed at 100 µL for each well of a 96-well ELISA plate (Nunc, Maxisorp), and the well was left standing for 6 hours at 4° C. to coat the cells. After washing three times with PBS, 300 µL of 1% rabbit serum/PBS was added to each well, and the well was left standing for 16 hours at 4° C. to perform blocking. Furthermore, after washing three times with 0.05% Tween 20/PBS, 100 µL/well of an immunized mouse serum or hybridoma culture supernatant was added to each well, and the well was left standing for 2 hours at 30° C. After washing three times with 0.05% Tween 20/PBS again, 100 µL/well of a goat HRP-labelled F(ab')$_2$ anti-mouse IgG+IgM (BioSource) or a goat HRP-labelled F(ab')$_2$ anti-mouse IgG (γ) (KPL) was added as the secondary antibody to each well, and the well was left standing for 2 hours at 30° C. After washing three times with 0.05% Tween 20/PBS, 100 µL/well of ABTS was added to each well as the substrate to allow color to develop, and photometry at $A_{405}$ was performed using a microplate reader to measure the amount of anti-*Staphylococcus* antibodies.

In this ELISA system using an anti-*Staphylococcus* mouse monoclonal antibody (isotype: IgG3, QED, BioScience) as the positive control primary antibody, and a mouse IgG (Chemicon) and a normal mouse serum as the negative controls, it was possible to detect the specific antibody of the positive control within the concentration range of 0.1 to 10 µg/mL.

Production of Anti-*Staphylococcus* Antibody-Producing Hybridomas

Three days after the final fifth immunization, splenocytes were collected, and polyethylene glycol was used to perform a cell-cell fusion with the mouse myeloma culture cell line SP2/0 to obtain hybridomas according to a conventional method.

As a result of the measurement of the anti-*Staphylococcus* IgG and IgM antibodies in the hybridoma culture supernatants using *Staphylococcus aureus* solid phase Cell-ELISA, antibodies having binding affinity to *Staphylococcus aureus* were detected in 106 of 1002 wells. Among them, 30 wells with $A_{405}$>2 were used for cloning, and by repeatedly screening using *Staphylococcus aureus* solid phase Cell-ELISA (IgG detection), and cloning by limiting dilution method, 22 hybridomas that produce anti-*Staphylococcus* antibodies were obtained.

Monoclonal Antibody Purification

For the preparation of monoclonal antibody samples for in vivo screening, purification/preparation was performed from hybridoma-induced ascitic fluids that could be expected to have an antibody content of several mg/mL.

A total of 5×10$^6$ hybridoma cells that reached the exponential growth phase were administered to the peritoneal cavity of a SCID mouse (CLEA Japan, Inc.), which is genetically/functionally B cell- and T cell-deficient and lacks immunoglobulins, and after one to two weeks, the accumulated ascitic fluid was collected and freeze-stored at −70° C.

After thawing, this was made into a 20% saturated ammonium sulfate solution and salted out to remove the fibrin protein, etc., then the supernatant was made into a 50% saturated ammonium sulfate solution, and salted out again, and the resulting precipitate was dissolved in 20 mM sodium phosphate-containing saline (pH 7.0). After passing the solution through a 0.45 µM filter, a buffer exchange to 20 mM phosphate buffered saline was performed with a Sephadex G25 column chromatography, and the resulting eluted sample solution was allowed to bind to a protein G affinity column. Elution of the bound antibodies was performed with 0.1M glycine-containing saline (pH 2.7), and the eluted purified antibody solution was immediately neutralized. This purified antibody solution was buffer exchanged to PBS and concentrated using a centrifugation ultrafiltration unit (Centricon Plus 20 PL-100, Nihon Millipore K.K.). After passing the solution through a 0.45 µM filter, a purified antibody solution with a concentration of 5 mg/mL was prepared based on $A_{280}$, and freeze-stored at −70° C.

Binding Affinity between Monoclonal Antibody and *Staphylococcus*

The binding affinity between an anti-*Staphylococcus* antibody and a *Staphylococcus* was examined by ELTSA reactivity.

When the reactivity of each purified antibody was examined by *Staphylococcus aureus* solid phase Cell-ELISA, four groups were observed based on their added concentration and reactivity (FIG. 2). The four groups were: first, the group of ZBIA6H, 8H, 10H, 11H, and 12H purified antibodies, which exhibited a very high binding affinity; second, the group of ZBIA2H, 4H, and 14H purified antibody, which exhibited the second highest binding affinity compared to the first group; third, the group that exhibited a moderate level of binding affinity and to which ZBIA1H, 3H, 5H, 7H, 9H, 13H, 15H, 16H, 17H, 19H, 20H, 21H, and 22H belong; and fourth, ZBIA18H with a weak binding affinity.

Example 2

Cross-Reactivity of Anti-*Staphylococcus* Antibodies

A freeze-stored *Staphylococcus epidermidis* strain ATCC12228 was grown by shaking culture for 16 hours at 37° C. in TSB. The culture medium was added in an amount of 1/100 to fresh TSB, and shaking culture further continued for 4 hours at 37° C. This was centrifuged, washed three times with PBS, and adjusted to a concentration of about $A_{600}=0.1$. This was dispensed at 100 μL for each well of a 96-well ELISA plate (Nunc, Maxisorp), and the well was left standing for 6 hours at 4° C. to coat the bacterial cells. After washing three times with PBS, 300 μL of 1% rabbit serum/PBS was added to each well, and the well was left standing for 16 hours at 4° C. to perform blocking. Furthermore, after washing three times with 0.05% Tween 20/PBS, 100 μL/well of the ZBIA5H antibody or ZBIA3H antibody was added, and the well was left standing for 2 hours at 30° C. After washing three times with 0.05% Tween 20/PBS again, 100 μL/well of a goat HRP-labelled F(ab')$_2$ anti-mouse IgG (γ) (KPL) was added as the secondary antibody, and the well was left standing for 2 hours at 30° C. After washing three times with 0.05% Tween 20/PBS, 100 μL/well of ABTS was added as the substrate to allow color to develop, and photometry at $A_{405}$ was performed using a microplate reader to measure the amount of anti-*Staphylococcus* antibodies exhibiting cross-reactivity with *Staphylococcus epidermidis*.

As a result, the above antibodies also exhibited binding affinity to *Staphylococcus epidermidis* (FIG. 3).

Example 3

Effects on a Community-Acquired MRSA Mouse Sepsis Model

The *Staphylococcus aureus* strain MW2, at $8 \times 10^8$ cells/0.5 mL PBS, and 0.2 mL of a test substance (PBS, 1 mg anti-*Staphylococcus* antibody, 1 mg mouse IgG) were administered to the peritoneal cavities of female 7-week-old BALB/c mice, and the number of surviving mice was determined.

As a result, the ZBIA5H antibody and ZBIA3H antibody exhibited significant life-prolonging effects compared to the PBS-administered group (Fisher's exact test; FIGS. 4 and 5).

Moreover, the group simultaneously administered with 0.5 mg of the ZBIA5H antibody and 0.5 mg of the ZBIA3H antibody exhibited a superior life-prolonging effect to the groups administered with 1 mg of the ZBIA5H antibody or 1 mg of the ZBIA3H antibody alone (FIG. 6).

Example 4

Effects on a Highly Vancomycin-Resistant MRSA Mouse Sepsis Model

The *Staphylococcus aureus* strain VRS1, at $2-3 \times 10^9$ cells/0.5 mL PBS, and 0.2 mL of a test sample (PBS, 1 mg anti-*Staphylococcus* antibody, 1 mg mouse IgG, 1 mg vancomycin hydrochloride (VCM)) were administered to the peritoneal cavities of female 7-week-old BALB/c mice, and the number of surviving mice was determined.

As a result, the ZBIA5H antibody and ZBIA3H antibody exhibited significant life-prolonging effects compared to the PBS-administered group and the VCM-administered group (Fisher's exact test; FIG. 7).

Example 5

Preventive Effect on a Community-Acquired MRSA Mouse Pneumonia Model

The *Staphylococcus aureus* strain MW2 used in the community-acquired MRSA mouse sepsis model in Example 3 is known to cause necrotizing pneumonia (Non-Patent Document 5). In order to elucidate the effectiveness on pneumonia of the ZBIA5H antibody and ZBIA3H antibody, which were effective in Examples 3 and 4, they were tested in a pneumonia prevention experiment.

A 0.2 mL portion of a test sample (PBS, 1 mg anti-*Staphylococcus* antibody, 1 mg vancomycin hydrochloride (VCM)) was administered into the tail vein, and one hour after the administration, the *Staphylococcus aureus* strain MW2 was nasally administered at $4 \times 10^8$ cells/40 μL PBS to female 7-week-old BALB/c mice to infect the lungs. Four days after the infection, the lungs were extirpated, suspended using a homogenizer, applied to mannitol salt agar plates, and cultured for 36 hours at 37° C. The number of colonies that appeared was counted, and was defined as the number of lung infecting bacteria.

Upon a statistical analysis of the obtained results using the Wilcoxon rank sum test, the ZBIA5H antibody- and ZBIA3H antibody-administered groups had significantly reduced numbers of lung infecting bacteria compared to the group administered with PBS (FIGS. 8 and 9).

Example 6

Therapeutic Effects on a Community-Acquired MRSA Mouse Pneumonia Model

Since the pneumonia-preventing effect of the ZBIA5H and ZBIA3H antibodies was confirmed in Example 5, the antibodies were next tested in a therapeutic experiment.

The *Staphylococcus aureus* strain MW2 was nasally administered, at $4 \times 10^8$ cells/40 μL PBS, to female 7-week-old BALB/c mice to allow the bacteria to infect the lungs. Three days later, 0.2 mL of a test sample (PBS, 1 mg anti-*Staphylococcus* antibody, 1 mg mouse IgG, 1 mg vancomycin hydrochloride (VCM)) was administered into the tail veins.

Five days after the *Staphylococcus aureus* administration (two days after the test sample administration), the lungs were extirpated, homogenized, and the resulting suspensions were applied to mannitol salt agar plates. They were cultured for 36 hours at 37° C. The number of colonies that appeared was counted, and was used as the number of lung infecting bacteria.

Upon a statistical analysis of the obtained results using the Wilcoxon rank sum test, the ZBIA5H antibody-, ZBIA3H antibody-, and VCM-administered groups had significantly reduced numbers of lung infecting bacteria compared to the group administered with PBS (FIGS. 10 and 11).

From the above experiments, these antibodies were confirmed to be useful in the prevention or treatment of staphylococcal infections.

Example 7

Cloning of Variable Regions of Antibodies

Genes for the variable regions in the ZBIA5H antibody and ZBIA3H antibody were obtained by 5'-RACE (Rapid Amplification of cDNA Ends).

First, all the RNAs were extracted from the hybridomas producing the ZBIA5H antibody or ZBIA3H antibody, and oligo-dT primers (Invitrogen) were used to synthesize cDNAs using a reverse transcriptase (SuperScript II; Invitrogen). In the presence of dCTP (Takara Bio Inc.), dCTPs (C-tail) were added to the cDNA 3' termini using TdT (terminal deoxynucleotidyl transferase; Toyobo Co., Ltd. or Takara Bio Inc.). The products were used as templates to amplify the genes for the heavy chain and light chain variable regions in the ZBIA5H antibody or ZBIA3H antibody by PCR, using an oligo-dG primer with a complementary sequence to the C tail, and a mouse κ chain gene-specific primer or a mouse heavy chain gene-specific primer. Each amplified product was subcloned into a p3T vector (Mo Bi Tec), and the DNA sequence of the introduced gene was confirmed. The amino acid sequences of the heavy chain and light chain variable regions are shown in FIG. 12 and FIG. 13.

Deposition of Hybridomas

An international deposit (based on the Budapest Treaty) was made for each of the hybridomas producing the following antibodies at National Institute of Technology and Evaluation (NITE) Patent Microorganisms Depository (2-5-8 Kazusakamatari, Kisarazu-shi, Chiba, Japan):

| Antibody | Hybridoma Accession Number | Date of Original Deposit | Date of Transfer to International Deposit |
|---|---|---|---|
| ZBIA5H | NITE BP-1367 | May 29, 2012 | Jun. 25, 2012 |
| ZBIA3H | NITE BP-1366 | May 29, 2012 | Jun. 25, 2012 |

The above various embodiments explained by the descriptions of modes for carrying out the invention have been disclosed with the intention to illustrate, but not to limit, the present invention. The technical scope of the present invention is defined by the recitations of the claims, and those skilled in the art can make various design changes in the technical scope of the invention recited in the claims.

Additionally, the disclosures of the patent, patent applications, and publications cited in the present specification are all incorporated herein by reference.

Accession Numbers

Hybridoma (ZBIA5H): NITE BP-1367
Hybridoma (ZBIA3H): NITE BP-1366

The invention claimed is:

1. An antibody, comprising:
   a heavy chain variable region that comprises
      (i) CDRH1 of SEQ ID NO: 1, CDRH2 of SEQ ID NO: 2, and CDRH3 of SEQ ID NO: 3 or
      (ii) CDRH1 of SEQ ID NO: 9, CDRH2 of SEQ ID NO: 10, and CDRH3 of SEQ ID NO: 11; and
   a light chain variable region that comprises
      (i) CDRL1 of SEQ ID NO: 4, CDRL2 of SEQ ID NO: 5, and CDRL3 of SEQ ID NO: 6 or
      (ii) CDRL1 of SEQ ID NO: 12, CDRL2 of SEQ ID NO: 13, and CDRL3 of SEQ ID NO: 14.

2. The antibody of claim 1, wherein
   the heavy chain variable region comprises CDRH1 of SEQ ID NO: 1, CDRH2 of SEQ ID NO: 2, and CDRH3 of SEQ ID NO: 3; and
   the light chain variable region comprises CDRL1 of SEQ ID NO: 4, CDRL2 of SEQ ID NO: 5, and CDRL3 of SEQ ID NO: 6.

3. The antibody of claim 2, comprising a heavy chain variable region that comprises the amino acid sequence of SEQ ID NO: 7, and a light chain variable region that comprises the amino acid sequence of SEQ ID NO: 8.

4. The antibody of claim 1, wherein
   the heavy chain variable region comprises CDRH1 of SEQ ID NO: 9, CDRH2 of SEQ ID NO: 10, and CDRH3 of SEQ ID NO: 11; and
   the light chain variable region comprises CDRL1 of SEQ ID NO: 12, CDRL2 of SEQ ID NO: 13, and CDRL3 of SEQ ID NO: 14.

5. The antibody of claim 4, comprising a heavy chain variable region that comprises the amino acid sequence of SEQ ID NO: 15, and a light chain variable region that comprises the amino acid sequence of SEQ ID NO: 16.

6. An Fab antibody fragment of the antibody of claim 1.

7. The antibody of claim 1, which is a chimeric antibody, a humanized antibody, or a human antibody.

8. An antibody produced by a hybridoma deposited under Accession Number: NITE BP-1367 or Accession Number: NITE BP-1366.

9. A humanized antibody version of the antibody of claim 8.

10. The antibody of claim 1, which is conjugated to an antimicrobial substance.

11. A nucleic acid encoding the antibody of claim 1.

12. A composition comprising the antibody of claim 2 and an antibody comprising:
    a heavy chain variable region that comprises CDRH1 of SEQ ID NO: 9, CDRH2 of SEQ ID NO: 10, and CDRH3 of SEQ ID NO: 11; and
    a light chain variable region that comprises CDRL1 of SEQ ID NO: 12, CDRL2 of SEQ ID NO: 13, and CDRL3 of SEQ ID NO: 14.

13. An article of manufacture, comprising:
    (a) a container;
    (b) a package insert and/or a label on the container; and
    (c) the composition of claim 12 held in the container; wherein at least one of the package insert and/or the label on the container indicates that the composition can be used to treat or prevent a staphylococcal infection.

14. A medicament for treating a staphylococcal infection, comprising the antibody of claim 1 and at least one of pharmaceutically acceptable carrier, a delivery medium, and a delivery carrier.

15. A medicament for treating a staphylococcal infection, comprising (i) the antibody of claim 2 and (ii) an antibody comprising:
    a heavy chain variable region that comprises CDRH1 of SEQ ID NO: 9, CDRH2 of SEQ ID NO: 10, and CDRH3 of SEQ ID NO: 11; and
    a light chain variable region that comprises CDRL1 of SEQ ID NO: 12, CDRL2 of SEQ ID NO: 13, and CDRL3 of SEQ ID NO: 14.

16. A nucleic acid encoding the antibody of claim 9.

17. A method for treating a staphylococcal infection, comprising administering to a subject in need thereof an effective amount of the antibody of claim 1.

18. A method for improving a subject's defense against future staphylococcal infection, comprising administering to a subject in need thereof an effective amount of the antibody of claim 1.

19. A chimeric antibody version of the antibody of claim 8.

* * * * *

```
                         SEQUENCE LISTING

<160> NUMBER OF SEQ ID NOS: 24

<210> SEQ ID NO 1
<211> LENGTH: 5
<212> TYPE: PRT
<213> ORGANISM: Mus musculus

<400> SEQUENCE: 1

Asp Tyr Ser Met His
1               5

<210> SEQ ID NO 2
<211> LENGTH: 17
<212> TYPE: PRT
<213> ORGANISM: Mus musculus

<400> SEQUENCE: 2

Trp Ile Asn Thr Glu Thr Gly Glu Pro Thr Tyr Ala Asp Asp Phe Lys
1               5                   10                  15

Gly

<210> SEQ ID NO 3
<211> LENGTH: 7
<212> TYPE: PRT
<213> ORGANISM: Mus musculus

<400> SEQUENCE: 3

Pro Tyr Tyr Ala Met Asp Tyr
1               5

<210> SEQ ID NO 4
<211> LENGTH: 11
<212> TYPE: PRT
<213> ORGANISM: Mus musculus

<400> SEQUENCE: 4

Lys Ala Ser Gln Asp Ile Asn Lys Tyr Ile Ala
1               5                   10

<210> SEQ ID NO 5
<211> LENGTH: 7
<212> TYPE: PRT
```

```
<213> ORGANISM: Mus musculus

<400> SEQUENCE: 5

Tyr Thr Ser Thr Leu Gln Pro
1               5

<210> SEQ ID NO 6
<211> LENGTH: 10
<212> TYPE: PRT
<213> ORGANISM: Mus musculus

<400> SEQUENCE: 6

Leu Gln Tyr Asp Asn Leu Leu Pro Trp Thr
1               5                   10

<210> SEQ ID NO 7
<211> LENGTH: 116
<212> TYPE: PRT
<213> ORGANISM: Mus musculus

<400> SEQUENCE: 7

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Met
            35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Pro Tyr Tyr Ala Met Asp Tyr Trp Gly Gln Gly Thr Ser Val
            100                 105                 110

Thr Val Ser Ser
        115

<210> SEQ ID NO 8
<211> LENGTH: 108
<212> TYPE: PRT
<213> ORGANISM: Mus musculus

<400> SEQUENCE: 8

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Pro
                85                  90                  95

Trp Thr Phe Gly Gly Gly Thr Lys Leu Glu Ile Lys
            100                 105
```

```
<210> SEQ ID NO 9
<211> LENGTH: 5
<212> TYPE: PRT
<213> ORGANISM: Mus musculus

<400> SEQUENCE: 9

Thr Tyr Ala Met Asn
1               5

<210> SEQ ID NO 10
<211> LENGTH: 19
<212> TYPE: PRT
<213> ORGANISM: Mus musculus

<400> SEQUENCE: 10

Arg Ile Arg Ser Lys Ser Asn Asn Tyr Ala Thr Tyr Tyr Ala Asp Ser
1               5                   10                  15

Val Lys Asp

<210> SEQ ID NO 11
<211> LENGTH: 12
<212> TYPE: PRT
<213> ORGANISM: Mus musculus

<400> SEQUENCE: 11

Arg Gly Gly Asn Ala Ile Tyr Tyr Ala Met Asp Tyr
1               5                   10

<210> SEQ ID NO 12
<211> LENGTH: 10
<212> TYPE: PRT
<213> ORGANISM: Mus musculus

<400> SEQUENCE: 12

Ser Ala Asn Ser Ser Val Ser Tyr Met His
1               5                   10

<210> SEQ ID NO 13
<211> LENGTH: 7
<212> TYPE: PRT
<213> ORGANISM: Mus musculus

<400> SEQUENCE: 13

Asp Thr Ser Lys Leu Ala Ser
1               5

<210> SEQ ID NO 14
<211> LENGTH: 9
<212> TYPE: PRT
<213> ORGANISM: Mus musculus

<400> SEQUENCE: 14

Gln Gln Trp Ser Ser Asn Pro Pro Thr
1               5

<210> SEQ ID NO 15
<211> LENGTH: 123
<212> TYPE: PRT
<213> ORGANISM: Mus musculus

<400> SEQUENCE: 15

Glu Val Gln Leu Val Glu Ser Gly Gly Gly Leu Val Gln Pro Lys Gly
1               5                   10                  15
```

```
Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
 50                  55                  60

Ser Val Lys Asp Arg Phe Thr Ile Ser Arg Asp Asp Ser Gln Ser Met
 65                  70                  75                  80

Leu Tyr Leu Gln Met Asn Ser Leu Lys Thr Glu Asp Thr Ala Met Tyr
                85                  90                  95

Tyr Cys Val Arg Arg Gly Gly Asn Ala Ile Tyr Tyr Ala Met Asp Tyr
                100                 105                 110

Trp Gly Gln Gly Thr Ser Val Thr Val Ser Ser
            115                 120

<210> SEQ ID NO 16
<211> LENGTH: 106
<212> TYPE: PRT
<213> ORGANISM: Mus musculus

<400> SEQUENCE: 16

Gln Ile Val Leu Thr Gln Ser Pro Ala Ile Met Ser Ala Ser Pro Gly
 1               5                  10                  15

Glu Lys Val Thr Met Thr Cys Ser Ala Asn Ser Ser Val Ser Tyr Met
            20                  25                  30

His Trp Tyr Gln Gln Lys Ser Gly Thr Ser Pro Lys Ala Trp Ile Tyr
            35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys
                100                 105

<210> SEQ ID NO 17
<211> LENGTH: 5
<212> TYPE: PRT
<213> ORGANISM: Mus musculus

<400> SEQUENCE: 17

Thr Tyr Ala Met Asn
 1               5

<210> SEQ ID NO 18
<211> LENGTH: 19
<212> TYPE: PRT
<213> ORGANISM: Mus musculus

<400> SEQUENCE: 18

Arg Ile Arg Ser Lys Ser Asn Asn Tyr Ala Thr Tyr Tyr Ala Asp Ser
 1               5                  10                  15

Val Lys Asp

<210> SEQ ID NO 19
<211> LENGTH: 11
<212> TYPE: PRT
<213> ORGANISM: Mus musculus
```

-continued

<400> SEQUENCE: 19

Arg Gly Gly Asn Pro Tyr Tyr Ala Met Asp Tyr
1               5                   10

<210> SEQ ID NO 20
<211> LENGTH: 10
<212> TYPE: PRT
<213> ORGANISM: Mus musculus

<400> SEQUENCE: 20

Arg Ala Ser Ser Val Ser Tyr Met His
1               5                   10

<210> SEQ ID NO 21
<211> LENGTH: 7
<212> TYPE: PRT
<213> ORGANISM: Mus musculus

<400> SEQUENCE: 21

Ala Thr Ser Asn Leu Ala Ser
1               5

<210> SEQ ID NO 22
<211> LENGTH: 9
<212> TYPE: PRT
<213> ORGANISM: Mus musculus

<400> SEQUENCE: 22

Gln Gln Trp Ser Ser Asn Pro Pro Thr
1               5

<210> SEQ ID NO 23
<211> LENGTH: 122
<212> TYPE: PRT
<213> ORGANISM: Mus musculus

<400> SEQUENCE: 23

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Phe Arg Asp Asp Ser Gln Ser Ile
65                  70                  75                  80

Leu Tyr Leu Gln Leu Asn Asn Leu Lys Thr Glu Asp Thr Ala Met Tyr
                85                  90                  95

Tyr Cys Val Arg Arg Gly Gly Asn Pro Tyr Tyr Ala Met Asp Tyr Trp
            100                 105                 110

Gly Gln Gly Thr Ser Val Thr Val Ser Ser
        115                 120

<210> SEQ ID NO 24
<211> LENGTH: 106
<212> TYPE: PRT
<213> ORGANISM: Mus musculus

<400> SEQUENCE: 24

-continued

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Gly Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
            85                  90                  95

Phe Gly Gly Gly Thr Lys Leu Glu Ile Lys
            100                 105
```